(12) United States Patent
Morriss et al.

(10) Patent No.: US 9,713,710 B2
(45) Date of Patent: Jul. 25, 2017

(54) SYSTEMS AND METHODS FOR ANESTHETIZING EAR TISSUE

(71) Applicant: Tusker Medical, Inc., Menlo Park, CA (US)

(72) Inventors: John H. Morriss, San Francisco, CA (US); Greg Liu, Sunnyvale, CA (US); Rohit Girotra, Mountain View, CA (US); Bernard H. Andreas, Redwood City, CA (US); Scott J. Baron, Redwood City, CA (US); Paul G. Hayter, Mountain View, CA (US); Thomas Jenkins, Oakland, CA (US); Richard R. Newhauser, Jr., Emerald Hills, CA (US); Jeffrey A. Walker, Livermore, CA (US)

(73) Assignee: Tusker Medical, Inc., Menlo Park, CA (US)

( * ) Notice: Subject to any disclaimer, the term of this patent is extended or adjusted under 35 U.S.C. 154(b) by 138 days.

(21) Appl. No.: 13/798,635

(22) Filed: Mar. 13, 2013

(65) Prior Publication Data

US 2013/0197426 A1 Aug. 1, 2013

Related U.S. Application Data

(63) Continuation of application No. 12/510,217, filed on Jul. 27, 2009, now Pat. No. 8,452,392.
(Continued)

(51) Int. Cl.
*A61N 1/30* (2006.01)
*A61M 1/00* (2006.01)
(Continued)

(52) U.S. Cl.
CPC .............. *A61N 1/306* (2013.01); *A61F 11/00* (2013.01); *A61M 1/0088* (2013.01);
(Continued)

(58) Field of Classification Search
CPC ...... A61F 11/00; A61F 11/002; A61F 11/004; A61F 11/006; A61F 11/008; A61F 11/08;
(Continued)

(56) References Cited

U.S. PATENT DOCUMENTS

| 858,673 A | 7/1907 | Roswell |
| 1,920,006 A | 7/1933 | Dozieb et al. |

(Continued)

FOREIGN PATENT DOCUMENTS

| CN | 86105171 | 3/1987 |
| CN | 2087067 U | 10/1991 |

(Continued)

OTHER PUBLICATIONS

Comeau, Maurice et al.; "Local Anesthesia of the Ear by Iontophoresis"; 1973, Arch Otolaryngol, vol. 98, pp. 114-120.
(Continued)

*Primary Examiner* — Kami A Bosworth

(57) ABSTRACT

A system and method for use in iontophoretic anesthesia of a tympanic membrane are disclosed. The system generally includes an earplug and an electrode device. The earplug includes at least one sealing member for sealing the earplug in an ear canal. The method involves using the system on a human or animal subject.

20 Claims, 27 Drawing Sheets

Related U.S. Application Data

(60) Provisional application No. 61/085,360, filed on Jul. 31, 2008.

(51) Int. Cl.
| | | |
|---|---|---|
| *A61F 11/00* | (2006.01) | |
| *A61M 19/00* | (2006.01) | |
| *A61N 1/04* | (2006.01) | |
| *A61N 1/36* | (2006.01) | |

(52) U.S. Cl.
CPC .............. *A61N 1/303* (2013.01); *A61M 19/00* (2013.01); *A61M 2205/3341* (2013.01); *A61M 2210/0662* (2013.01); *A61N 1/044* (2013.01); *A61N 1/36021* (2013.01)

(58) Field of Classification Search
CPC .... A61F 11/10; A61F 11/12; A61F 2011/085; A61N 1/30; A61N 1/303; A61N 1/306
USPC ........... 600/379; 604/20, 21, 164.02, 164.04, 604/167.06; 606/109, 162
See application file for complete search history.

(56) References Cited

U.S. PATENT DOCUMENTS

| | | | |
|---|---|---|---|
| 2,458,884 A | 1/1949 | Volkmann | |
| 3,741,197 A | 6/1973 | Sanz et al. | |
| 3,888,258 A | 6/1975 | Akiyama | |
| 3,897,786 A | 8/1975 | Garnett et al. | |
| 3,913,584 A | 10/1975 | Walchle et al. | |
| 3,948,271 A | 4/1976 | Akiyama | |
| 3,991,755 A | 11/1976 | Vernon et al. | |
| 4,149,533 A | 4/1979 | Ishikawa et al. | |
| 4,406,282 A | 9/1983 | Parker et al. | |
| 4,468,218 A | 8/1984 | Armstrong | |
| 4,473,073 A | 9/1984 | Darnell | |
| 4,552,137 A | 11/1985 | Strauss | |
| 4,564,009 A | 1/1986 | Brinkhoff | |
| 4,601,294 A * | 7/1986 | Danby ................... | A61B 5/042 600/379 |
| 4,712,537 A | 12/1987 | Pender | |
| 4,968,296 A | 11/1990 | Ritch et al. | |
| 4,971,076 A | 11/1990 | Densert et al. | |
| 5,026,378 A | 6/1991 | Goldsmith, III | |
| 5,044,373 A | 9/1991 | Northeved et al. | |
| 5,047,007 A | 9/1991 | McNichols et al. | |
| 5,053,040 A | 10/1991 | Goldsmith, III | |
| 5,107,861 A | 4/1992 | Narboni | |
| 5,135,478 A | 8/1992 | Sibalis | |
| 5,160,316 A | 11/1992 | Henley | |
| 5,254,081 A | 10/1993 | Maurer et al. | |
| 5,254,120 A | 10/1993 | Cinberg et al. | |
| 5,261,903 A | 11/1993 | Dhaliwal et al. | |
| D352,780 S | 11/1994 | Glaeser et al. | |
| 5,421,818 A | 6/1995 | Arenberg | |
| 5,466,239 A | 11/1995 | Cinberg et al. | |
| 5,496,329 A | 3/1996 | Reisinger | |
| D378,611 S | 3/1997 | Croley | |
| 5,610,988 A | 3/1997 | Miyahara | |
| 5,643,280 A | 7/1997 | Del Rio et al. | |
| 5,674,196 A * | 10/1997 | Donaldson .......... | A61M 3/0262 604/174 |
| D387,863 S | 12/1997 | Herman et al. | |
| 5,707,383 A | 1/1998 | Bays et al. | |
| 5,792,100 A | 8/1998 | Shantha | |
| 5,827,295 A | 10/1998 | Del Rio et al. | |
| 5,893,828 A | 4/1999 | Uram | |
| D418,223 S | 12/1999 | Phipps et al. | |
| D420,741 S | 2/2000 | Croley | |
| 6,045,528 A | 4/2000 | Arenberg et al. | |
| D424,197 S | 5/2000 | Sydlowski et al. | |
| 6,059,803 A | 5/2000 | Spilman | |
| D426,135 S | 6/2000 | Lee | |
| 6,137,889 A | 10/2000 | Shennib et al. | |
| 6,148,821 A * | 11/2000 | Falco ..................... | A61F 11/08 128/864 |
| 6,183,469 B1 | 2/2001 | Thapliyal et al. | |
| 6,200,280 B1 | 3/2001 | Brenneman et al. | |
| 6,206,888 B1 | 3/2001 | Bicek et al. | |
| 6,245,077 B1 | 6/2001 | East et al. | |
| 6,251,121 B1 | 6/2001 | Saadat | |
| 6,295,469 B1 | 9/2001 | Linkwitz et al. | |
| D450,843 S | 11/2001 | McGuckin, Jr. et al. | |
| 6,347,246 B1 | 2/2002 | Perrault et al. | |
| 6,358,231 B1 | 3/2002 | Schindler et al. | |
| 6,440,102 B1 * | 8/2002 | Arenberg ................ | A61F 11/00 604/506 |
| 6,475,138 B1 | 11/2002 | Schechter et al. | |
| 6,512,950 B2 | 1/2003 | Li et al. | |
| 6,514,261 B1 | 2/2003 | Randall et al. | |
| 6,520,939 B2 | 2/2003 | Lafontaine | |
| 6,522,827 B1 | 2/2003 | Loeb et al. | |
| 6,553,253 B1 | 4/2003 | Chang | |
| 6,640,121 B1 | 10/2003 | Telischi et al. | |
| 6,645,173 B1 | 11/2003 | Liebowitz | |
| 6,648,873 B2 | 11/2003 | Arenberg et al. | |
| 6,663,575 B2 | 12/2003 | Leysieffer | |
| 6,682,558 B2 | 1/2004 | Tu et al. | |
| 6,770,080 B2 | 8/2004 | Kaplan et al. | |
| 6,916,159 B2 | 7/2005 | Rush et al. | |
| 7,123,957 B2 | 10/2006 | Avrahami | |
| 7,127,285 B2 | 10/2006 | Henley et al. | |
| 7,137,975 B2 | 11/2006 | Miller et al. | |
| D535,027 S | 1/2007 | James et al. | |
| 7,160,274 B2 | 1/2007 | Ciok et al. | |
| 7,344,507 B2 | 3/2008 | Briggs et al. | |
| 7,351,246 B2 | 4/2008 | Epley | |
| 7,381,210 B2 | 6/2008 | Zarbatany et al. | |
| D595,410 S | 6/2009 | Luzon | |
| 7,563,232 B2 | 7/2009 | Freeman et al. | |
| D598,543 S | 8/2009 | Vogel et al. | |
| 7,654,997 B2 | 2/2010 | Makower et al. | |
| 7,677,734 B2 | 3/2010 | Wallace | |
| 7,704,259 B2 | 4/2010 | Kaplan et al. | |
| 7,749,254 B2 | 7/2010 | Sobelman et al. | |
| D622,842 S | 8/2010 | Benoist | |
| 8,052,693 B2 | 11/2011 | Shahoian | |
| 8,192,420 B2 | 6/2012 | Morriss et al. | |
| 8,249,700 B2 | 8/2012 | Clifford et al. | |
| 8,409,175 B2 | 4/2013 | Lee et al. | |
| 8,425,488 B2 | 4/2013 | Clifford et al. | |
| 8,452,392 B2 | 5/2013 | Morriss et al. | |
| 8,498,425 B2 | 7/2013 | Graylin | |
| 8,518,098 B2 | 8/2013 | Roeder et al. | |
| 8,702,722 B2 | 4/2014 | Shahoian | |
| 8,840,602 B2 | 9/2014 | Morriss et al. | |
| 8,849,394 B2 | 9/2014 | Clifford et al. | |
| 9,011,363 B2 | 4/2015 | Clopp et al. | |
| 9,023,059 B2 | 5/2015 | Loushin et al. | |
| 9,216,112 B2 | 12/2015 | Clifford et al. | |
| 9,364,648 B2 | 6/2016 | Girotra et al. | |
| 9,387,124 B2 | 7/2016 | Clifford | |
| 9,392,229 B2 | 7/2016 | Morriss et al. | |
| 2002/0026125 A1 | 2/2002 | Leysieffer | |
| 2002/0069883 A1 | 6/2002 | Hirchenbain | |
| 2002/0111585 A1 | 8/2002 | Lafontaine | |
| 2002/0138091 A1 | 9/2002 | Pflueger | |
| 2002/0161379 A1 | 10/2002 | Kaplan et al. | |
| 2002/0169456 A1 | 11/2002 | Tu et al. | |
| 2003/0060799 A1 | 3/2003 | Arenberg et al. | |
| 2003/0093057 A1 | 5/2003 | Zhang et al. | |
| 2003/0199791 A1 | 10/2003 | Boecker et al. | |
| 2004/0054339 A1 | 3/2004 | Ciok et al. | |
| 2005/0094835 A1* | 5/2005 | Doty .............................. | 381/328 |
| 2005/0182385 A1 | 8/2005 | Epley | |
| 2005/0235422 A1 | 10/2005 | Wallace | |
| 2005/0240147 A1 | 10/2005 | Makower et al. | |
| 2006/0142700 A1 | 6/2006 | Sobelman et al. | |
| 2006/0155304 A1 | 7/2006 | Kaplan et al. | |
| 2006/0177080 A1* | 8/2006 | Smith ..................... | A61F 11/08 381/313 |
| 2007/0078372 A1 | 4/2007 | Reddy et al. | |

(56) References Cited

U.S. PATENT DOCUMENTS

| | | | |
|---|---|---|---|
| 2007/0183613 A1* | 8/2007 | Juneau | A61F 11/10 381/322 |
| 2007/0233222 A1 | 10/2007 | Roeder et al. | |
| 2008/0011308 A1 | 1/2008 | Fleming | |
| 2008/0051804 A1 | 2/2008 | Cottler et al. | |
| 2008/0058756 A1 | 3/2008 | Smith | |
| 2008/0107287 A1 | 5/2008 | Beard | |
| 2008/0212416 A1 | 9/2008 | Polonio et al. | |
| 2008/0262468 A1 | 10/2008 | Clifford et al. | |
| 2008/0262508 A1 | 10/2008 | Clifford et al. | |
| 2008/0262510 A1 | 10/2008 | Clifford | |
| 2009/0163848 A1 | 6/2009 | Morriss et al. | |
| 2009/0209972 A1 | 8/2009 | Loushin et al. | |
| 2009/0262510 A1 | 10/2009 | Pekkarinen et al. | |
| 2009/0270807 A1* | 10/2009 | Mas | A61B 17/22 604/119 |
| 2009/0299344 A1 | 12/2009 | Lee et al. | |
| 2010/0030131 A1 | 2/2010 | Morriss et al. | |
| 2010/0041447 A1 | 2/2010 | Graylin | |
| 2010/0061581 A1 | 3/2010 | Soetejo et al. | |
| 2010/0198135 A1 | 8/2010 | Morriss et al. | |
| 2010/0300460 A1 | 12/2010 | Falco et al. | |
| 2011/0001564 A1 | 1/2011 | Hori | |
| 2011/0015645 A1 | 1/2011 | Liu et al. | |
| 2011/0048414 A1 | 3/2011 | Hoekman et al. | |
| 2011/0268303 A1 | 11/2011 | Ahsani | |
| 2011/0288559 A1 | 11/2011 | Shahoian | |
| 2012/0310145 A1 | 12/2012 | Clifford et al. | |
| 2013/0090544 A1 | 4/2013 | Clifford et al. | |
| 2013/0190678 A1 | 7/2013 | Andreas et al. | |
| 2013/0223702 A1 | 8/2013 | Holsing et al. | |
| 2014/0102461 A1 | 4/2014 | Girotra et al. | |
| 2014/0194891 A1 | 7/2014 | Shahoian | |
| 2014/0276352 A1 | 9/2014 | Kermani et al. | |
| 2014/0276906 A1 | 9/2014 | Andreas et al. | |
| 2015/0068539 A1 | 3/2015 | Morriss et al. | |

FOREIGN PATENT DOCUMENTS

| | | |
|---|---|---|
| CN | 2409940 Y | 12/2000 |
| DE | 19618585 | 11/1997 |
| EP | 0214527 | 3/1987 |
| FR | 2526656 | 11/1983 |
| JP | 59-129815 | 8/1984 |
| JP | H 07-116190 A | 5/1995 |
| JP | 2010-524584 | 7/2010 |
| JP | 58-21431 | 11/2015 |
| WO | WO 92/10223 | 6/1992 |
| WO | WO 2006/119512 | 11/2006 |
| WO | WO2008/030485 | 3/2008 |
| WO | WO 2008/036368 | 3/2008 |
| WO | WO 2008/131195 | 10/2008 |
| WO | WO 2009/010788 | 1/2009 |
| WO | WO 2010/014894 | 2/2010 |
| WO | WO 2011/081772 | 7/2011 |
| WO | WO 2013/016098 | 1/2013 |
| WO | WO 2013/181009 | 12/2013 |
| WO | WO 2014/158543 | 10/2014 |

OTHER PUBLICATIONS

Comeau, Maurice et al.; "Anesthesia of the Human Tympanic Membrane by Iontophoresis of a Local Anesthetic"; 1978, The Larynoqoscope, vol. 88, pp. 277-285.
Echols, Dean F. et al.; "Anesthesia of the Ear by Iontophoresis of Lidocaine"; 1975, Arch Otolaryngol, vol. 101, pp. 418-421.
Epley, John M.; "Modified Technique of Iontophoretic Anesthesia for Myringotomy in Children"; 1977, Arch Otolaryngol, vol. 103, pp. 358-360.
Hasegawa, M. et al.; "Iontophoretic anaesthesia of the tympanic membrane"; 1978, Clinical Otolaryngoloy, vol. 3, pp. 63-66.
Medtronic XOMED. Activent.RTM., Antimicrobial Ventilation Tubes. 4 pages.
Micromedics Innovative Surgical Products [retrieved on Jul. 15, 2010] Retrieved from the Internet <URL: http://www.micromedics-usa.com/products/otology/micromedicstubes.htm. 7 pages.
Plenum Compact Oxford English Dictionary.
Plenum Merriam-Webster's Online Dictionary, 11th edition.
Ramsden, R.T. et al.; "Anaesthesia of the tympanic membrane using iontophoresis"; 1977, The Journal of Laryngology and Otology, vol. 56, No. 9, pp. 779-785.
International Search Report dated Sep. 3, 2008 for Application No. PCT/US2008/60779.
International Search Report dated Nov. 6, 2009 for Application No. PCT/US2009/052395.
International Search Report dated Jun. 30, 2010 for Application No. PCT/US2009/069388.
International Search Report dated Aug. 27, 2010 for Application No. PCT/US2010/042128.
International Search Report dated Feb. 17, 2011 for Application No. PCT/US2010/058718.
Russian Office Action dated May 24, 2013 for Application No. RU 2011-072228.
U.S. Appl. No. 61/085,360, filed Jul. 31, 2008.
English Machine Translation of Chinese Patent No. CN 86105171.
English Machine Translation of French Patent No. FR 2526656.
English Machine Translation of German Patent No. DE 19618585.
U.S. Appl. No. 60/912,902, filed Apr. 19, 2007.
Patent Examination Report No. 1 for Australian Patent Application No. 2008242735, dated Aug. 8, 2012, 3 pages.
Patent Examination Report No. 1 for Australian Patent Application No. 2013209354, dated Oct. 13, 2014, 5 pages.
First Office Action for Chinese Patent Application No. 200880020861.9, dated Jul. 12, 2011, 10 pages.
Second Office Action for Chinese Patent Application No. 200880020861.9, dated Dec. 31, 2011, 3 pages.
Search Report for Chinese Patent Application No. 201310047126.X, dated Mar. 6, 2015, 2 pages.
Second Office Action for Chinese Patent Application No. 201310047126.X, dated Mar. 16, 2015, 3 pages.
Office Action for European Application No. 08746237.0, mailed Mar. 24, 2016, 3 pages.
Office Action for European Application No. 08746237.0, mailed Aug. 4, 2015, 7 pages.
Supplementary Partial Search Report for European Application No. 08746237.0, mailed Jun. 30, 2014, 9 pages.
Notification of Reasons for Refusal for Japanese Patent Application No. 2010-504267, dated Nov. 20, 2012, 4 pages.
Notification of Reasons for Refusal for Japanese Patent Application No. 2010-504267, dated Nov. 12, 2013, 4 pages.
Written Opinion for International Application No. PCT/US2008/060779, mailed Sep. 3, 2008.
Office Action for U.S. Appl. No. 11/749,733, mailed Jun. 10, 2009, 13 pages.
Office Action for U.S. Appl. No. 11/749,733, mailed Dec. 2, 2008, 9 pages.
Patent Examination Report No. 1 for Australian Application No. 2009276384, dated Apr. 14, 2014, 3 pages.
Office Action for Canadian Application No. 2,732,595, dated Dec. 8, 2015, 4 pages.
Office Action for U.S. Appl. No. 12/510,217, mailed Feb. 28, 2012, 17 pages.
Office Action for U.S. Appl. No. 12/510,217, mailed Aug. 9, 2012, 16 pages.
Written Opinion for International Application No. PCT/US2009/052395, mailed Nov. 6, 2009.
Patent Examination Report No. 1 for Australian Application No. 2010337214, dated Feb. 27, 2015, 3 pages.
Office Action for U.S. Appl. No. 12/650,469, mailed Oct. 2, 2013, 8 pages.
Office Action for U.S. Appl. No. 12/650,469, mailed Aug. 10, 2012, 12 pages.
Office Action for U.S. Appl. No. 12/650,469, mailed Jan. 9, 2013, 12 pages.
Written Opinion for International Application No. PCT/US2010/058718, mailed Feb. 17, 2011.

(56) References Cited

OTHER PUBLICATIONS

Office Action for Australian Application No. 2012287268, dated Feb. 11, 2016.
Office Action for European Application No. 12743007.2, mailed Jul. 21, 2016, 5 pages.
Notification of Reasons for Refusal for Japanese Application No. 2014-522882, mailed May 31, 2016, English Translation.
International Search Report for International Application No. PCT/US2012/047179, mailed Mar. 11, 2013.
Written Opinion for International Application No. PCT/US2012/047179, mailed Mar. 11, 2013.
First Office Action for Chinese Patent Application No. 201380027926.3, dated May 3, 2016.
International Search Report for International Application No. PCT/US2013/041816, mailed Sep. 16, 2013, 14 pages.
Written Opinion for International Application No. PCT/US2013/041816, mailed Sep. 16, 2013, 14 pages.
International Search Report and Written Opinion for International Application No. PCT/US2014/018017, mailed May 22, 2014, 12 pages.
Chinese Office Action dated Mar. 31, 2016, for corresponding Application No. CN 201080065012.2, 12 pages (English translation).
Office Action for U.S. Appl. No. 13/647,562, mailed Dec. 1, 2016, 14 pages.
Office Action for European Application No. 10793367.3, Nov. 11, 2016, 4 pages.
Office Action for Korean Application No. 10-2012-7019894 dated Feb. 6, 2017, 7 pages.
Offfice Action for U.S. Appl. No. 14/464,884, mailed Aug. 9, 2016, 22 pages.
Office Action for Australian Application No. 2013267734, dated Nov. 8, 2016, 4 pages.
Office Action for Chinese Application No. 201380027926.3, issued Jan. 16, 2017.
Official Action for U.S. Appl. No. 13/804,491, mailed Dec. 1, 2016, 19 pages.
International Search Report and Written Opinion for Application No. PCT/US2016/042577, mailed Dec. 6, 2016.

* cited by examiner

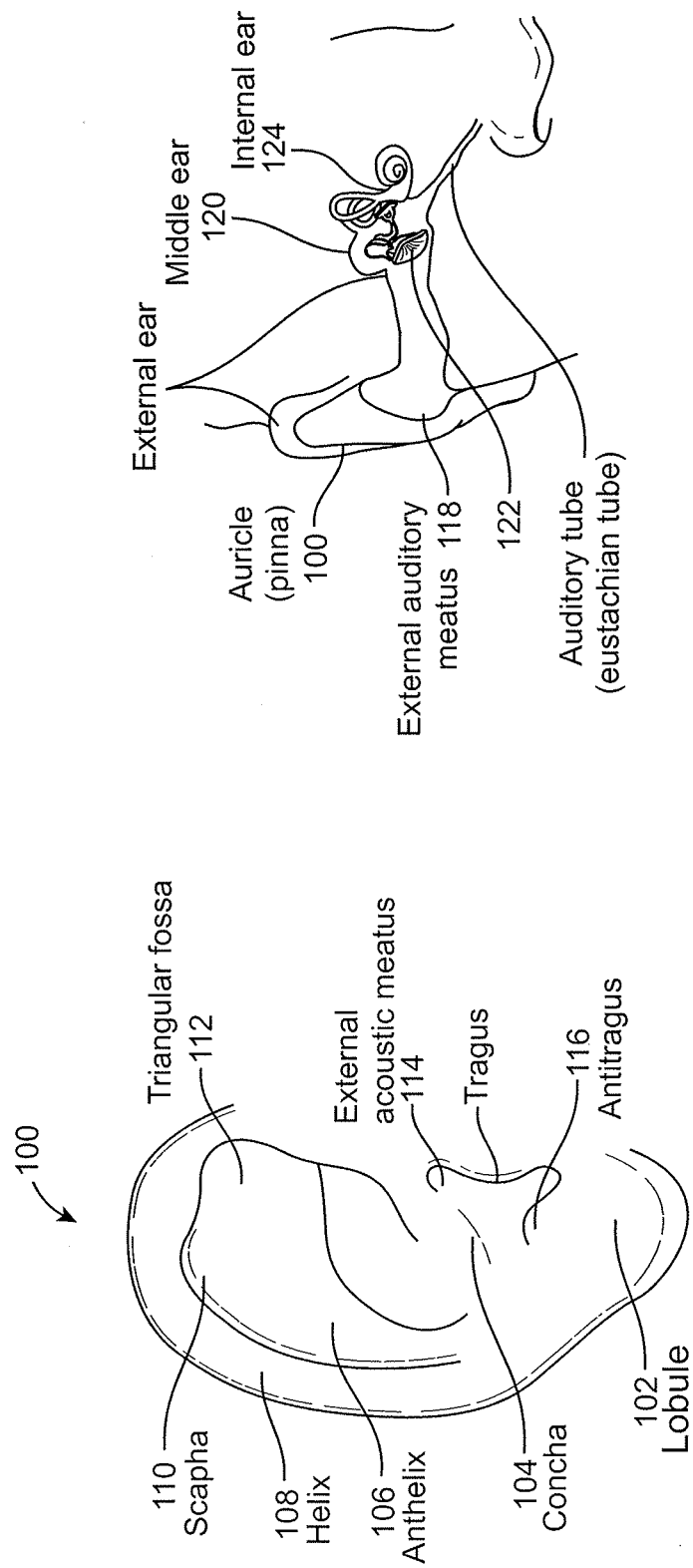

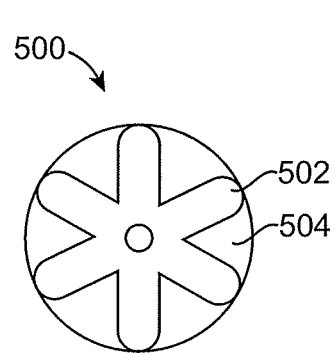
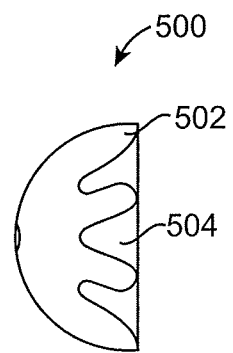
FIG. 5A    FIG. 5B
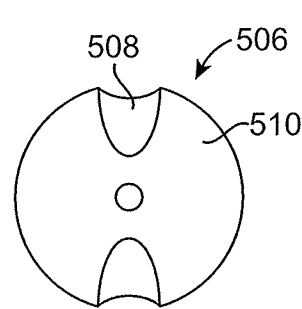
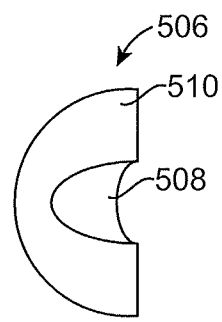
FIG. 5C    FIG. 5D

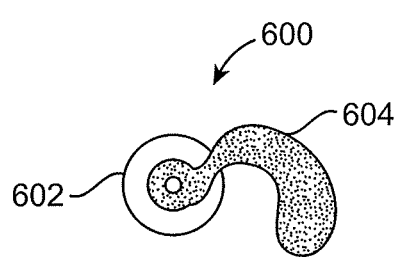
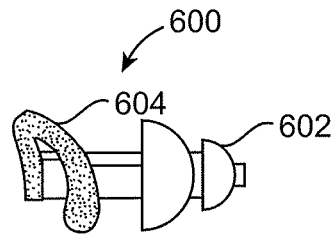
FIG. 6A  FIG. 6B
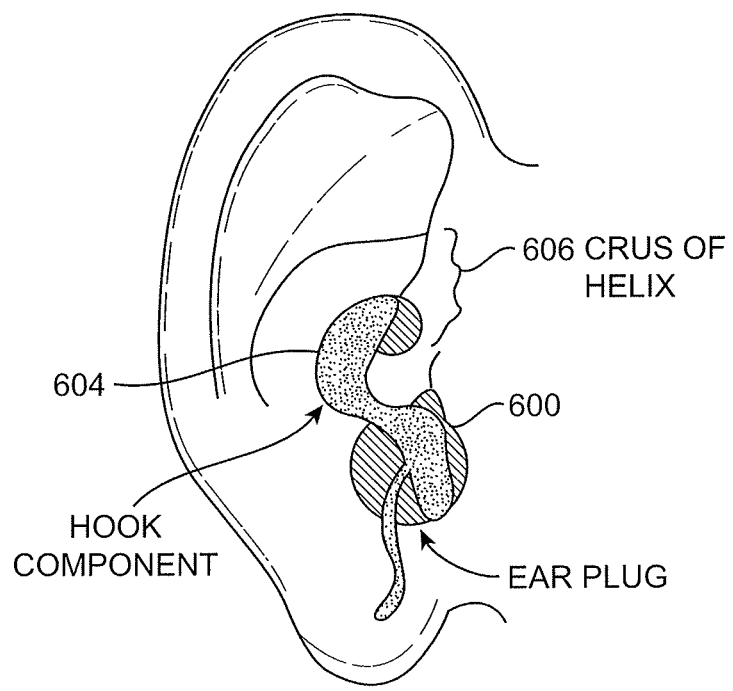
FIG. 6C

SYSTEMS AND METHODS FOR ANESTHETIZING EAR TISSUE

CROSS-REFERENCES TO RELATED APPLICATIONS

This application is a continuation of U.S. application Ser. No. 12/510,217, filed Jul. 27, 2009, now U.S. Pat. No. 8,452,392, which claims the benefit of U.S. Provisional Application No. 61/085,360, entitled "SYSTEMS AND METHODS FOR ANESTHETIZING EAR TISSUE", filed on Jul. 31, 2008, the entirety of which is incorporated by reference herein.

FIELD OF THE INVENTION

The present invention is related to iontophoretic drug delivery methods and systems. In particular, the present invention is related to novel and advantageous iontophoretic drug delivery methods and systems for anesthetizing ear tissue.

BACKGROUND OF THE INVENTION

Iontophoresis is a method for delivering a drug across a biological membrane, such as the skin or, in the case of certain ear surgery procedures, the tympanic membrane (TM). By applying low-level electrical current to a similarly charged drug solution, iontophoresis repels ions of the drug, thus transporting them across the skin or other membrane. In ear procedures, attempts have been made in the past to use iontophoresis to anesthetize (or "numb") a TM before placing an ear tube across it to treat chronic ear infections. For TM iontophoresis, a drug solution is placed in an ear canal and current is applied to the solution via an electrode, thus transporting the anesthetizing drug across the TM.

Prior iontophoresis devices and systems have had limited success and often cannot be used in all patients. Prior devices generally do not seal the drug solution in an ear canal, thus requiring a patient to recline and tilt his/her head during an iontophoresis procedure. Using currently available iontophoresis methods, the patient must remain relatively motionless in this reclined, head-tilted position for 5-15 minutes while the iontophoresis procedure provides adequate anesthesia to the TM, which can be especially difficult for children. Furthermore, using the currently available systems it is only possible to anesthetize one ear at a time, thus making iontophoretic anesthesia of both TMs in a patient a relatively lengthy, uncomfortable process.

Attempts have been made to administer iontophoretic fluid to a TM via an earplug designed to hold the fluid in the ear canal. For example, see U.S. Pat. No. 5,674,196, issued to Donaldson et al. Earplugs such as the one described in Donaldson and other currently available earplugs, however, have a number of shortcomings. For example, most earplugs are designed to keep fluid out of the ear canal, rather than in the ear canal. Currently available and previously described earplugs generally do not conform adequately to the curved anatomy of the ear canal and thus to not form a good seal in the ear canals of at least some (and in some cases all) patients. Thus, current earplugs typically allow fluid to leak out of the ear, which makes iontophoretic anesthesia delivery difficult if not impossible with the patient in an upright position. Furthermore, previously described earplug devices for use in iontophoresis have not addressed issues such as bubble formation in the iontophoretic drug solution, which bubbles may interfere with the contact between an iontophoretic electrode and the solution.

Therefore, it would be advantageous to have improved devices and systems for administering iontophoresis to a tympanic membrane. Ideally, such devices and systems would allow iontophoretic anesthesia to be administered to a patient in an upright position. Also ideally, such devices and systems would facilitate bilateral, simultaneous TM iontophoresis. At least some of these objectives will be met by the embodiments of the present invention.

BRIEF SUMMARY OF THE INVENTION

In one aspect of the present invention, an iontophoresis system for anesthetizing the tympanic membrane of an ear of a patient may include an earplug, at least one flexible sealing element, and an electrode device. The earplug may include an distal portion, an proximal portion, a tube connecting the distal and proximal portions, and a side vent located at the tube or the proximal portion. The tube may have a relative stiffness that is less than that of the distal and proximal portions, the lower relative stiffness allowing the tube to conform to the curvature of an ear canal. The flexible sealing element may be coupled to the tube of the earplug and may be shaped to form a seal within the ear canal. The electrode may include an electrode tip and an elongate shaft and may be slideably disposable within the tube of the earplug, wherein the electrode tip is sized to fit within the distal portion and slide within the tube.

In one embodiment the earplug may include a side vent in fluid communication with the tube for allowing venting of air and/or fluid from the tube. In one embodiment the distal portion may be rigid relative to the tube. In one embodiment the distal portion may include an o-ring which seals against the electrode tip of the electrode device in the advanced position. In one embodiment an outer diameter of the electrode tip may be greater than an internal diameter of the o-ring, and the o-ring may be flexible to allow the electrode tip to pass into it to a seal. In one embodiment the proximal portion may be rigid. In one embodiment the proximal portion may include a luer fitting. In one embodiment the at least one flexible sealing element may be umbrella shaped, with an open end of the sealing element facing the proximal end of the earplug. In one embodiment the at least one flexible sealing element may include a distal sealing element and a proximal sealing element, and a diameter of the proximal sealing element may be larger than a diameter of the distal sealing element. In one embodiment each of the flexible sealing elements may be umbrella shaped, with an open end of each sealing element facing the proximal end of the earplug. In one embodiment the electrode device may be malleable. In one embodiment the electrode device may include a lumen. In one embodiment the system may include an ear hook connected with the proximal portion of the earplug, the ear hook including a curved member for engaging a portion of the ear and preventing dislodgement of the earplug after placement in the ear. In one embodiment the system may include an additional earplug and an additional electrode for use in iontophoretic substance delivery to the tympanic membrane of the other ear of the human or animal subject. In one embodiment the system may include a headset for coupling the earplug and the additional earplug while they are in the subject's ears.

In one aspect of the invention, a system for use in iontophoretic substance delivery to the tympanic membrane of an ear of a human or animal subject may include an elongate, flexible tube with a proximal portion and a distal portion, a first flexible sealing element shaped like an umbrella to form a seal within the ear canal, a second flexible sealing element shaped like an umbrella to form a seal within the ear canal, a distal stiffening tube located within the distal portion of the elongate tube distal to the sealing member, a luer fitting coupled with the proximal portion of the tube and including a side vent in fluid communication with the main lumen of the tube, and an electrode device. The flexible tube may include a main lumen extending therethrough. The distal portion may include an inner lip at the distal end of the distal portion and a sealing member proximal to the inner lip. The elongate tube may have sufficient flexibility to bend to conform to the shape of an ear canal. The first flexible sealing element may be integral to and disposed on an exterior of the elongate tube and being offset a distance from a distal most portion of the elongate tube. The second flexible sealing element may be integral to and disposed on the exterior of the elongate tube and proximal to the first sealing element. The distal stiffening tube may prevent the distal portion of the elongate tube from bending. The electrode device may include an elongate shaft. The electrode tip may have a diameter greater than that of the elongate shaft. The electrode device may be movable within the tube lumen of the earplug from a retracted position, in which fluid may pass around the electrode through the tube, to an advanced position, in which the electrode tip may fit within the distal portion of the elongate tube between the inner lip and the sealing member to form a fluid tight seal.

In one aspect of the present invention, a method of anesthetizing a tympanic membrane of an ear of a patient using iontophoresis may involve delivering an anesthetizing drug solution to an ear canal of the patient, inserting a iontophoresis device into the ear canal filled with anesthetizing drug solution, venting excess anesthetizing drug solution through the lumen while inserting and while the electrode is in the first position, moving the electrode from the first position to the second position, and activating the electrode in the second position. The iontophoresis device may include an electrode moveable from a first position to a second position inside a lumen. The first position of the iontophoresis device may vent the ear canal. The second position of the iontophoresis device may seal the ear canal.

In one embodiment the method may further include verifying moving the electrode from the first position to the second position using auditory and/or tactile feedback. In one embodiment the method may include repeating the method for a second ear of the subject. In one embodiment a head of the subject may be positioned in a reclined, tilted position when delivering the drug solution to the ear canal and an upright position when activating the electrode. In one embodiment the method may include repeating the method for a second ear of the subject, coupling the earplugs with a headset coupled with the subject's head before or during activating. In one embodiment the method may include deforming the electrode to conform it to a shape of the ear canal.

In one aspect of the invention, a method of anesthetizing a tympanic membrane of an ear of a patient using iontophoresis may include delivering an anesthetizing drug solution to an ear canal of the patient, inserting a iontophoresis device into an ear canal of the patient, and activating the electrode. The iontophoresis device may include an electrode inside a lumen. The iontophoresis device may seal the anesthetizing drug solution and simultaneously vents excess anesthetizing drug solution past the electrode and through a seal inside the lumen.

In one embodiment the method may include repeating the method for a second ear of the patient. In one embodiment the patient may be in a sideways position when delivering and an upright position when activating. In one embodiment the method may include deforming the electrode to conform to the shape of the ear canal.

In one aspect of the invention, a kit for anesthetizing a tympanic membrane of an ear of a human or animal subject using iontophoresis, the kit may include an earplug and a controller. The earplug may include a distal portion, a proximal portion, and a tube extending from the distal portion to the proximal portion, at least one flexible sealing element extending from an outer surface of the tube and disposed closer to the distal end than the proximal end, and an electrode device. The tube may have a stiffness less than a stiffness of the proximal and distal portions of the earplug. The electrode device may include an elongate shaft, and an electrode tip having a diameter greater than that of the elongate shaft. The electrode device may be movable within the tube of the earplug from a retracted position, in which fluid can pass around the electrode through the tube, to an advanced position, in which the electrode tip contacts an inner surface of the tube to prevent fluid from flowing through the tube. The controller may be electrically connectable to the electrode device.

In one embodiment the kit may include an additional earplug for the other ear of the subject, and an additional electrode device for the additional earplug. In one embodiment the controller may connect to the electrode device and the additional electrode device. In one embodiment the kit may include a headset for placing on the subject's head and holding the electrodes and earplugs. In one embodiment the kit may include a sufficient amount of drug solution to provide iontophoretic anesthesia to the tympanic membranes of both ears of the subject. In one embodiment the kit may include a drug delivery device for delivering the drug solution into the ear canals of the subject.

For further understanding of the nature and advantages of the various aspects and embodiments, reference should be made to the following description and accompanying drawing figures. Each of the figures is provided for the purpose of illustration and description only and is not intended to limit the scope of the embodiments of the present invention.

BRIEF DESCRIPTION OF THE DRAWINGS

FIG. 1A shows a frontal view of an outer ear.

FIG. 1B shows a partial cross-sectional view of an outer, middle, and inner ear.

FIG. 5A shows a frontal view of a flexible sealing element, according to one embodiment of the invention.

FIG. 5B shows a side view of a flexible sealing element, according to one embodiment of the invention.

FIG. 5C shows a frontal view of a flexible sealing element, according to one embodiment of the invention.

FIG. 5D shows a side view of a flexible sealing element, according to one embodiment of the invention.

FIG. 6A shows a front view of an earplug including an ear hook, according to one embodiment of the invention.

FIG. 6B shows a front view of an earplug including an ear hook, according to one embodiment of the invention.

FIG. 6C shows a facing view of an earplug including an ear hook in use, according to one embodiment of the invention.

DETAILED DESCRIPTION OF THE INVENTION

Figure 2A:
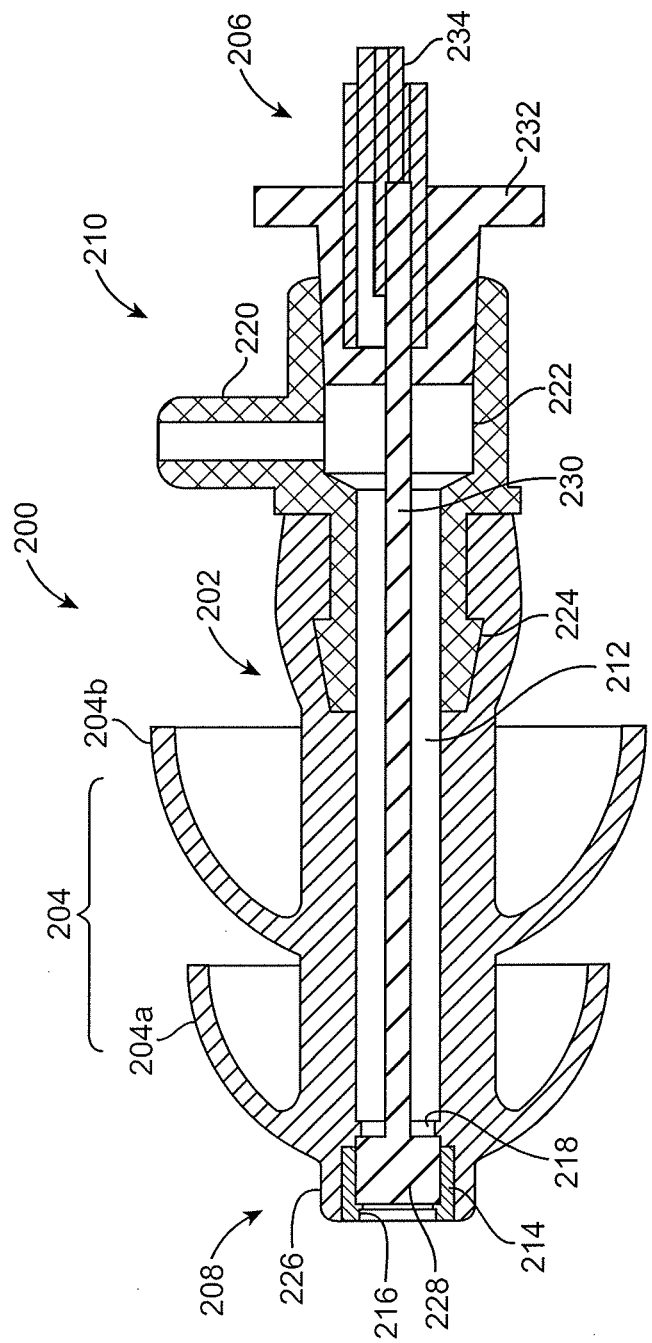
FIGS. 2A-2C show cross-sectional views of a system for anesthetizing a tympanic membrane, according to various embodiments of the invention.

FIG. 1A shows a view of an outer ear. The outer ear includes a major element known as the auricle or pinna 100. The outer ear serves as a funnel for directing sounds into the internal portions of the ear. The major physical features of the ear include the lobule 102, concha 104, anthelix 106, helix 108, scapha 110, triangular fossa 112, external acoustic meatus 114, tragus 116, and antitragus 118.

FIG. 1B shows a cross-section of the inner and outer portions of the ear. The pinna 100 is shown connected to the external auditory meatus 118, or ear canal. The ear canal 118 is shown as a relatively straight passage, but is often a more curved, tortuous passageway. The ear canal 118 is connected to the middle ear 120, which includes the ear drum 122. The middle ear 120 in turn is connected to the internal ear 124. The ear drum 122 normally has a pocket of air behind an outer portion called the tympanic membrane. When the middle ear 120 becomes infected, fluid swells inside the ear drum 122. Fluid expansion causes extreme pain to one with a middle ear infection. Middle ear infections are common in young children. Suffering may be alleviated by puncturing the tympanic membrane to evacuate the fluid, a treatment known as tympanocentesis. The patient may undergo general anesthesia prior to a tympanocentesis procedure, but this is not preferred due to cost and health concerns. As a preferable alternative, the tympanic membrane can be locally anesthetized using iontophoretic drug delivery. Thus the patient may be treated while awake. Devices and methods for locally anesthetizing the tympanic membrane are disclosed in co-assigned patent applications U.S. Ser. No. 11/962,073 and U.S. Ser. No. 11/749,729, the entireties of which are incorporated by reference herein.

FIG. 2A shows an iontophoresis system 200 for anesthetizing a tympanic membrane, according to one embodiment of the invention. The system 200 includes an earplug 202 and an electrode device 206. The earplug 202 may include a flexible sealing element 204, a distal portion 208, a proximal portion 210, and a tube 212 connecting both. The tube 212 is relatively more flexible, in terms of resistance to bending, than the distal portion 208 and proximal portion 210. This is particularly advantageous because the ear canal often is a tortuous passage, which requires that the distal portion 208 and proximal portion 210 to be placed at opposite ends of the tortuous passage. The earplug 202 will preferably bend and match the form of the tortuous passage without blocking the tube 212. Alternatively the earplug 202 may be pre-bent or pre-formed in a preferred shape to match a tortuous passage of an ear canal. To achieve a desired flexibility, the earplug 202 can be formed from a flexible polymer material, such as silicone.

The distal portion 208 can include a rigid member 214. The rigid member 214 can generally be cylindrical or tube shaped and include an inner lip 216 that prevents the electrode device from exiting the distal portion 208. The rigid member 214 can be constructed from a metal or polymer which adds structural integrity to the distal portion 208. The rigid member 214 provides the distal portion 208 to have a greater stiffness than the tube 212, such that the distal portion 208 will maintain shape when passed through a tortuous passage. The rigid member 214 can be bonded or molded into the distal portion 208 Alternatively, the rigid member 214 is integral to the distal portion 208 as a portion of wall thickness which is greater than the wall thickness of the tube 212.

The distal portion 208 can also include an o-ring 218. The o-ring 218 fluidly seals the electrode device 206 inside the distal portion 208. The o-ring can be bonded or molded into the distal portion 208, or alternatively be integrally formed between the distal portion 208 and the tube 212. The o-ring 218 can be designed to allow fluid to pass when experiencing a higher than atmosphere pressure load, e.g. the pressure which occurs from inserting the system 200 into a fluid filled ear. For example, the o-ring 218 can be designed as a duck-bill seal which opens into the proximal direction. It has been found in testing that 2.2 cm of H2O is a good value for threshold o-ring pressure relief.

The proximal portion 210 may be stiffer than the tube 212 such that the shape of the proximal portion 210 will be maintained when being inserted into a tortuous passage. The proximal portion 210 can include a side vent 220. The side vent 220 functions to vent excess fluid out of the ear, which vents from the proximal portion 208 and through the tube 212. Alternatively the side vent 220 may be located about the tube 212. The proximal portion 210 may include a luer fitting with a fluid tight fitting 222 to interface with the electrode device 206, as shown. The proximal portion may include a barbed portion 222 to interface with the tube 212. Alternatively the proximal portion 210 may be integrally formed into the tube 212, and maintain rigidity through molded stiffening inserts or by use of thick wall sections.

The flexible sealing elements 204 are used to form a fluid tight seal between the system 200 and the ear canal. The flexible sealing elements 204 are generally flexible and deform and conform to the shape of an ear canal to form a fluid tight seal. Two flexible sealing elements 204 are shown, however only one is required and more than two may be used. The first sealing element 204a may be oval-umbrella shaped and integrally formed into the tube 212 and distal portion 208, as shown. Alternatively the flexible sealing elements 204 may be pyramidal (three-sided) or triangular in shape. It has been found that the ear canal often has an oval or triangular cross-section. An offset 226 between the first flexible sealing element 204a and the distal most portion of the system 200 is preferred. The offset 226 provides extra volume inside the ear for air bubbles to reside, thus preventing air bubbles from blocking the distal portion 208. The second sealing element 204b may be larger than the first sealing element and integrally formed into the tube 212, as shown.

In an alternative embodiment, the flexible sealing elements 204 can include adhesive elements to promote a fluid tight seal between the surface of the sealing elements 204 and the ear canal. For example, an adhesive layer can be used on the external (i.e., canal facing) surfaces of the first sealing element 204a and/or the second sealing element 204b. The adhesive layer can be covered by a backing tape, which can be removed prior to insertion into the ear canal. A variety of adhesives can be used, for example, a temperature dependent adhesive which is only mildly tacky at room temperature and becomes extremely tacky after insertion through heating by the ear canal. A temperature dependent adhesive may allow for placement and replacement in the complex anatomy of the ear to minimize patient discomfort. The earplug 202 can be cooled by a cool compress to reduce tackiness and allow removal of the earplug 202. Examples of adhesive elements include the Eakin Cohesive® seal manufactured by CovaTec, Inc., and the Pre-Po® drape manufactured by Landec Labs, Inc. Alternatively, a temperature dependent adhesive which is extremely tacky at body temperature and becomes mildly tacky when heated to a temperature above body temperature can be used. In this embodiment, heat can be applied by a warm compress to reduce tackiness and allow removal of the earplug 202.

The electrode device 206 includes an electrode tip 228, an elongate shaft 230, and a proximal connector 232. The electrode tip 228 may be cylindrically shaped to match the interior portion of the distal portion 208. The electrode tip 228 is generally shaped to form a seal within the distal portion 208 between the inner lip 216 and the o-ring 218. The electrode tip 228 is also sized to be slideably disposable within the tube 212. The electrode tip 228 is preferably constructed from silver (99.9% pure). It has been found that a pure silver electrode tip 228, which may include an oxidized layer on the electrode tip 228, aids in the iontophoresis procedure. Prior devices utilized stainless steel or gold electrodes which have the tendency to cause electrolysis of an iontophoresis fluid, for example lidocaine, which in turn lowers the pH value and causes discomfort. The silver electrode relatively reduces electrolysis and prevents thus discomfort. Alternatively the electrode tip 228 may include a silver coating over a different metal such as stainless steel.

The electrode tip 228 is shown as a cylindrical shaped metal mass, however in alternative embodiments the electrode tip 228 can have different configurations to increase surface area and promote iontophoresis. For example, a plurality of silver wires configured similarly to a brush can be used. In another embodiment, a plurality of concentric hypotubes with staggered diameters can be used. In another embodiment, a silver mesh mass configured similarly to steel wool can be used. In another embodiment, a molded polymer matrix plug with a relatively large surface area (e.g., sponge like) and a gold or silver plating or deposition can be used. In another embodiment, a metal-coated woven fabric can be used, with or without an outer insulator depending on size. In another embodiment, a cylindrical body with an internal and distally exposed honeycomb can be used. In another embodiment, a silver foil coil can be used. In another embodiment, a recessed plug sized (i.e., smaller diameter) such that the plug has exposed sides can be used. In another embodiment, the elongate shaft 230 can be used as the electrode, either as a tube or wire, and using a proximal seal in the tube 212. In another embodiment, a mass with a plurality of petals or branches (e.g., flower shaped) which are integrated into the surface of a flexible sealing element 204 can be used. In another embodiment, a soft flexible bag, with an insulative outer surface and a silver coated inner surface, extending distally from the distal portion 208 can be used. In another embodiment, one or more cavities, which include metal coated surfaces, in the distal portion 208 may be used. In another embodiment, the electrode tip 228 can include holes and/or a textured surface (e.g., crosshatched, etched, sandblasted) to increase surface area. In another embodiment, the electrode tip 228 can include multiple metal types with one metal being a sacrificial anode (e.g., zinc). In another embodiment, a conveyor system (e.g., a metal coated flexible belt) which can be actuated to supply a fresh electrode surface throughout the procedure can be used. In another embodiment, the tube 212 can include wiping elements which clean the surface of an electrode when turned, in order to supply a fresh electrode surface throughout the procedure. In another embodiment, the electrode tip 228 can include a protective coating to help prevent corrosion.

The electrode tip 228 may be attached to the elongate shaft 230 by soldering or welding. The elongate shaft 230 may be constructed from the same materials as the electrode tip 228. The elongate shaft 230 may also include a lumen to allow the passage of fluid. The elongate shaft 230 is preferably malleable to allow a user to pre-bend the elongate shaft before inserting the system 200 into an ear canal. The earplug 202 may also be placed prior to the electrode device 206, and thus the electrode device 206 may be shaped to conform to the pre-inserted and deformed earplug 202. The proximal connector 232 is shaped to fluidly seal with the proximal portion 210. The proximal connector 232 is further electrically connected to a wire 234 to provide energy to the electrode device 206.

Figure 2B:
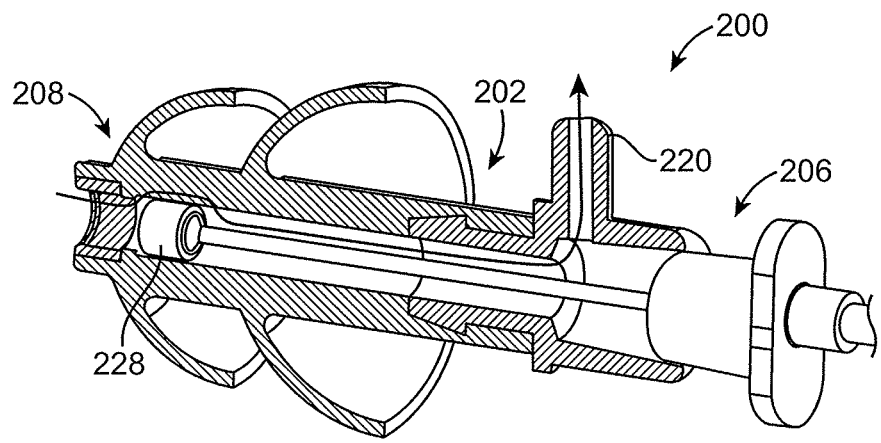

FIG. 2B shows the iontophoresis system 200 in a first position, according to one embodiment of the invention. The electrode device 206 is shown with the electrode tip 228 in a proximal position inside the tube 212. In the first position the distal portion 208 is in fluid communication with the tube 212. In the first position fluid may pass through the distal portion 208 and out through the vent 220, as shown by the directional arrow.

Figure 2C:
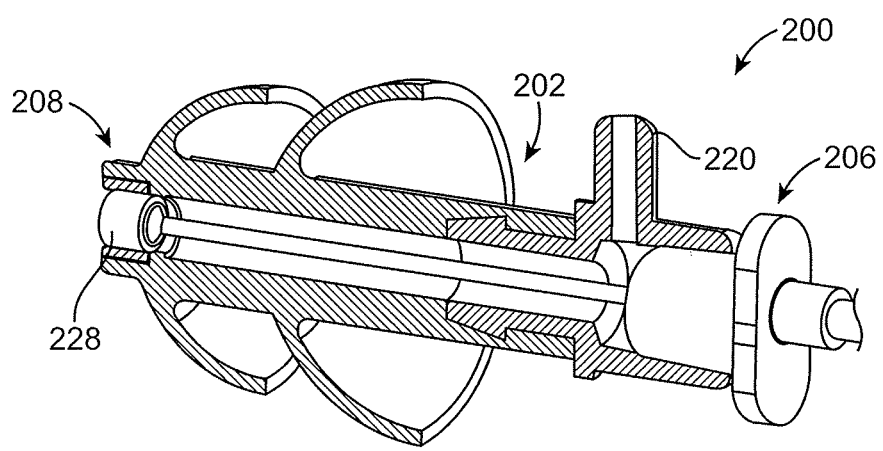

FIG. 2C shows the iontophoresis system 200 in a second position, according to one embodiment of the invention. The electrode device 206 is shown with the electrode tip in a distal position within the distal portion 208. The electrode device 206 may be forcibly passed by the o-ring 218 which may cause an audible 'snap'. Thus the electrode device 206 may be moved from the first position to the second position with an audible confirmation. In the second position the open distal position 208 is closed and is no longer in fluid communication with the tube 212. In an alternative embodiment the o-ring 218 may allow fluid to pass through when fluid pressures inside the ear canal exceed a threshold.

Figure 2D:
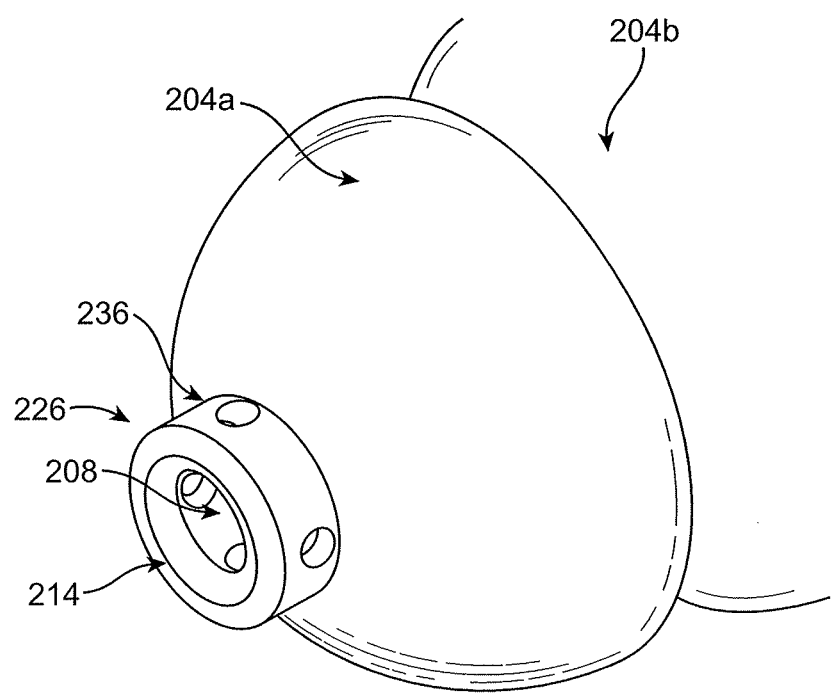
FIG. 2D shows a perspective view of a distal end of an earplug, according to one embodiment of the invention.

FIG. 2D shows an alternative embodiment of the iontophoresis system 200. In this embodiment, the offset portion 226 and distal portion 208 each include a plurality of aligned holes 236 which are placed proximately behind the inner lip 216. Four holes 236 are shown, however, more or fewer holes may be used in alternative embodiments. The holes 236 may have any of a number of suitable sizes, for example in one embodiment they may have diameters of about 0.025 inches each. The holes 236 can reduce trapped volume of the drug solution and allow more surface area of the electrode tip 228 to be exposed, which in turn can decrease the voltage requirement for an iontophoresis procedure. An iontophoresis procedure gradually causes the electrode tip 228 to corrode, and thus draw more voltage from an iontophoresis system as the electric efficiency of the electrode tip decreases. It has been experimentally shown in cadaver testing that the holes 236 can reduce voltage requirements by approximately two-thirds over a period of 10 minutes, as compared to a system 200 without holes 236. Thus, use of the holes 236 can prevent system checks and voltage spikes from occurring. System checks are instances where the iontophoresis system cannot meet the voltage demands of the corroded electrode tip 228, and thus the iontophoresis procedure can be unintentionally halted. Voltage spikes can cause discomfort to the patient.

Figure 2E:
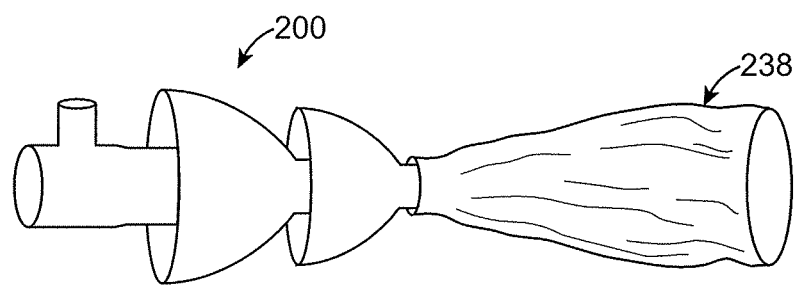
FIG. 2E shows a side view of an earplug, according to one embodiment of the invention.

FIG. 2E shows an alternative embodiment of the iontophoresis system 200. In this embodiment the system 200 remains largely as described above, however, a bag 238 is attached to the distal end of the system 200. The bag 238 may be constructed from a pliable substance such as a thin polymer or woven material. The bag 238 can have an outer adhesive substance, such as the adhesive members described herein. Organic debris, such skin flakes or wax can be dislodged during the insertion and/or iontophoresis process. The debris can stick to the electrode of the system 200 and reduce the active surface area of the electrode. In use, the system may be inserted into the ear and the bag 238 can be adhered to the surfaces of the ear canal leading up to the ear drum 122. The bag 238 can be expanded against the ear canal by physical probing with a probe such as a cotton swab, or inflated using expanding foam or a balloon. In some embodiments the bag 238 can be a double walled balloon. The bag 238 can prevent debris from sticking to the electrode by presenting a physical barrier between the ear canal and the electrode. The bag can also reduce the loss of drug solution, as the walls of the ear canal will be blocked from absorption of drug solution.

Figure 2F:
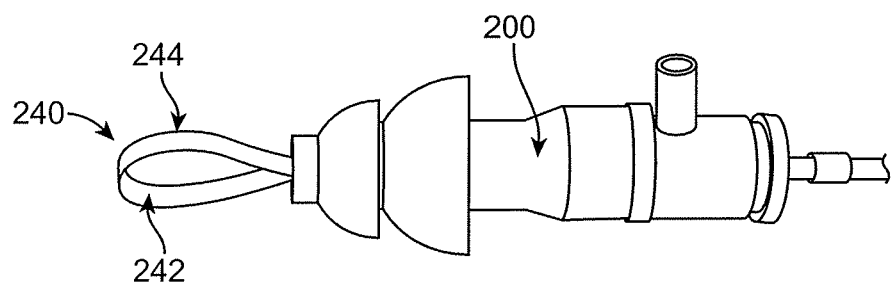
FIGS. 2F and 2G show side views of systems for anesthetizing a tympanic membrane, according to various embodiments of the invention.
Figure 2G:
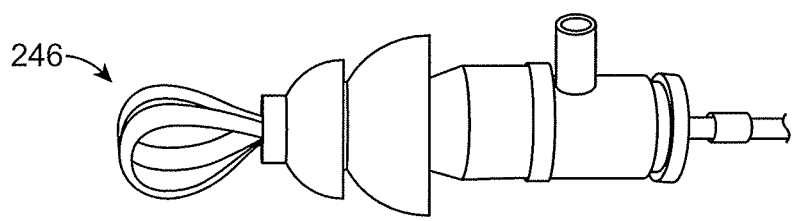
Figure 2H:
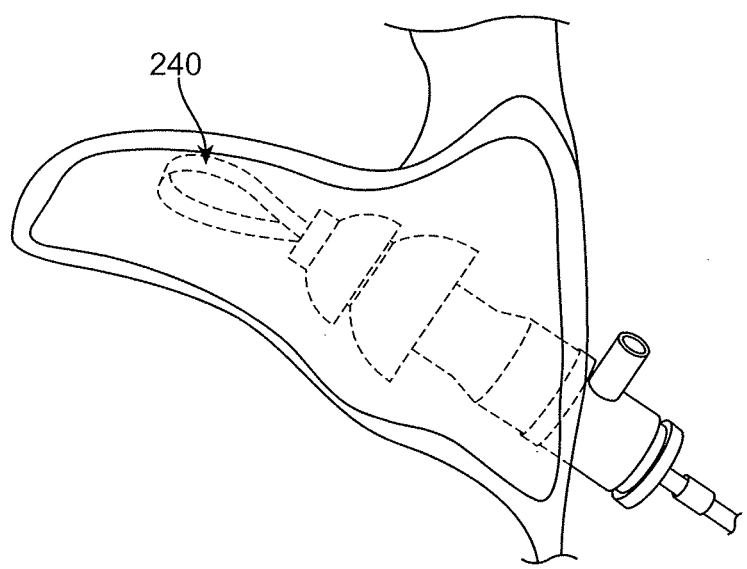
FIG. 2H shows a system in use, according to one embodiment of the invention.

FIGS. 2F through 2H show alternative embodiments of the iontophoresis system 200. In these embodiments, the system 200 remains largely as described above, however, a flexible electrode 240 extends from the distal end of the system 200. The flexible electrode 240 can include an insulative side 242, and a conductive side 244 with an exposed metal (e.g., silver) portion. The flexible electrode 240 can be constructed from a flexible polymer material, such as polyimide, and coextruded with a metal strip. The flexible electrode 240 can be configured as a singular looped band with the exposed metal portion on the inner portion of the loop. Alternatively, more than one band can be used, as shown by flexible electrode 246 of FIG. 2G. The length of extension of the flexible electrode 240 can be adjusted according to a specific patient's anatomy. In use, the flexible electrode 240 can come into contact with the ear canal, as shown in FIG. 2H, without causing shocks, as the conductive side 244 does not contact the ear canal. The flexible electrode 204 can deflect from the ear canal due to its flexible nature. The flexible electrode 240 provides a larger electrode surface area for a more efficient iontophoresis procedure. The large electrode surface area can also reduce bubble formation in the drug solution.

Figure 3A:
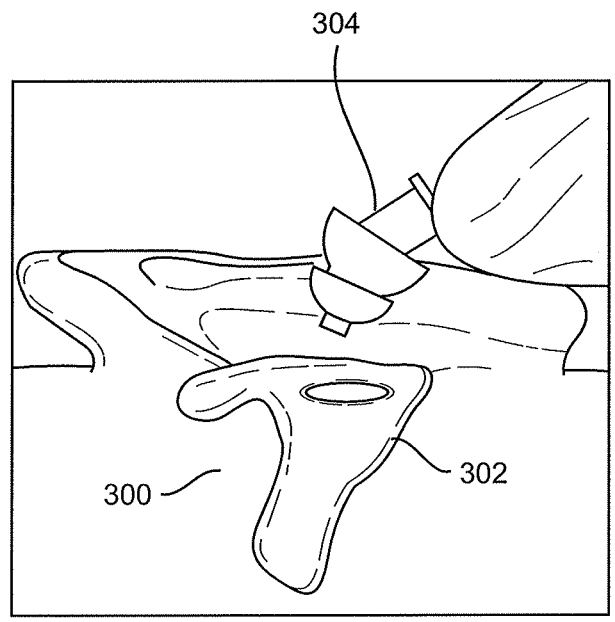
FIGS. 3A-3C show partial cross-sectional views of a system for anesthetizing a tympanic membrane in use, according to various embodiments of the invention.
Figure 3B:
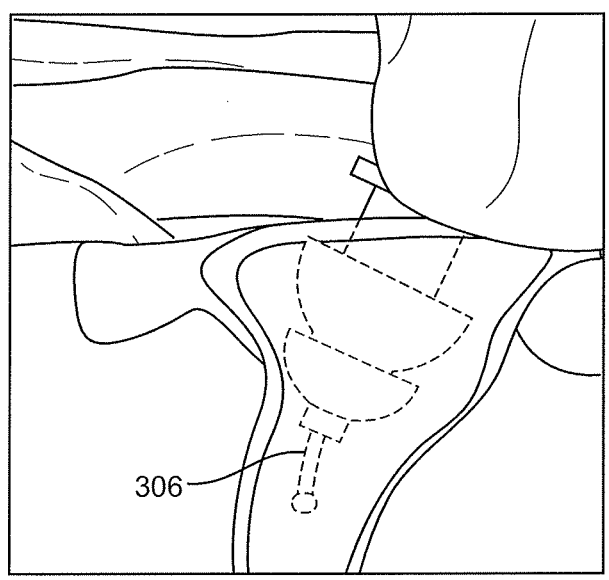
Figure 3C:
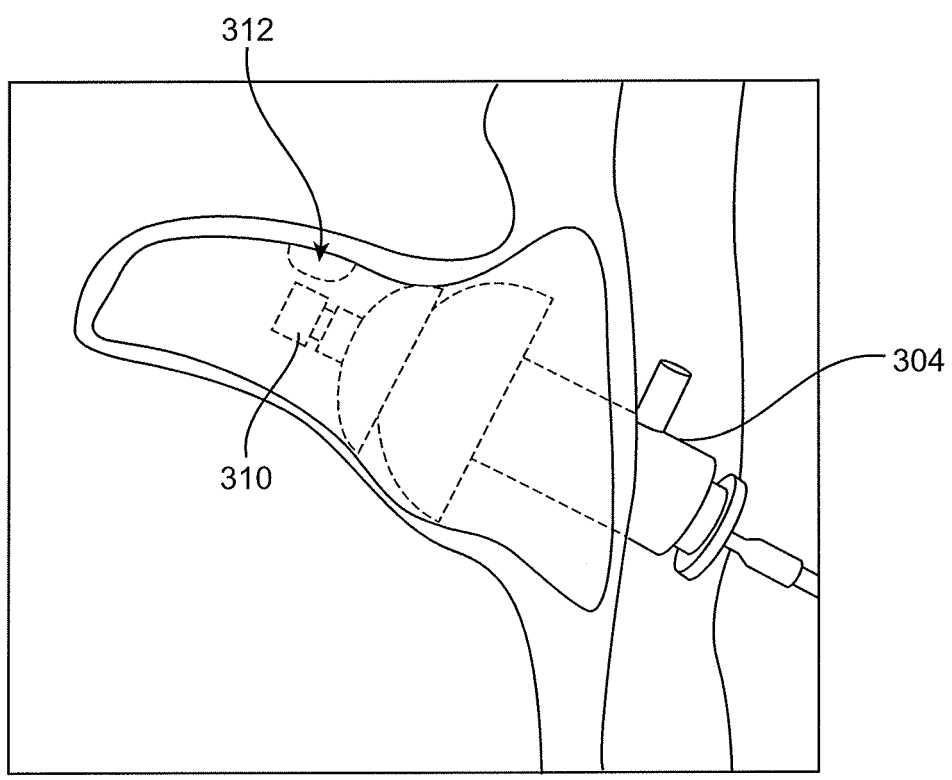

FIGS. 3A through 3C show a method of using the iontophoresis system 200 for anesthetizing a tympanic membrane of an ear of a patient, according to one embodiment of the invention. A cross-section of an ear 300 of a patient is shown. The patient may initially be placed on his or her side with the treatment ear facing upwards. Iontophoresis fluid 302 is then injected inside the ear canal, as shown. An earplug 304 is then inserted into the filled ear canal to seal the iontophoresis fluid within the ear canal. The earplug 304 is generally as described in the embodiments herein. The earplug 304 may optionally be primed with iontophoresis fluid 302 prior to inserting it into the ear canal.

In FIG. 3B, an electrode device 306 is inserted into the inserted earplug 304. The electrode device 306 may be malleable and optionally pre-bent prior to insertion. The electrode device 306 may make an audible noise when it is fully inserted into the earplug 304, thus giving the user an audible signal to verify that the electrode device is properly placed. As the electrode device 306 is fully inserted, pressure will increase inside the ear canal and excess fluid 308 will vent out the back of the plug and immediately balance the fluid pressure with the atmosphere, as shown. This is extremely advantageous, as even a slight pressure increase can cause great pain to an infected ear. After the electrode device 306 has been fully inserted, it may be energized to treat the patient. The other ear may also be treated as described herein.

In an alternative embodiment the electrode device 306 may be partially inserted into the earplug 304 in a first position, for example the electrode tip 228 in the tube 212, during the initial insertion into the ear canal. After the earplug 304 has been placed the electrode device 306 may be moved from the first position to a second position (e.g. working position) of full insertion into the earplug 304.

In yet another alternative embodiment the electrode device 306 may be fully inserted into the earplug 304 prior to insertion into the ear canal. As the earplug 304 is inserted into the ear canal, pressure will increase inside the ear, and simultaneously the pressure will be relieved through a seal within the earplug 304 which vents excess fluid when the pressure exceeds a certain threshold. This embodiment is advantageous because it does not require a user to move the electrode while the earplug is placed within the ear.

FIG. 3C shows the ear, and thus the patient, in an upright position. The device 304 includes an offset 310 from the electrode which causes air bubble 312 to move to the position shown. The offset 310 prevents air bubbles from resting directly or partially on the electrode, which would cause a partial or ineffective treatment. The offset 310 is advantageous because it allows the system 200 to be used in an upright position, and accordingly both ears may be treated simultaneously.

In an alternative embodiment the patient may be in an upright position prior to insertion of iontophoresis fluid 302 or the earplug 304. The earplug 304 is first inserted into the ear canal with the electrode device 306 fully inserted. In this embodiment the electrode device 306 includes a separate lumen for filling the ear canal. Iontophoresis fluid 302 is injected through the electrode device 306 to fill the ear canal. When the ear canal is filled with iontophoresis fluid 302, pressure will increase inside the ear, and simultaneously the pressure will be relieved through a seal within the earplug 304. Thus, excess fluid is vented when the pressure exceeds a certain threshold. This embodiment is advantageous because one or both ears may be filled simultaneously if required, and also while the patient is in an upright position.

In an alternative embodiment, a proximal sealing material can be applied after the device 304 is placed as shown in FIG. 3C. The sealing material can be made from soft, putty-like material, for example, a bone wax (e.g., beeswax, paraffin, or isopropyl palmitate) can be used. The sealing material can be used separately, or as a sealably attached member to the device 304, for example, as a proximally (e.g., between sealing member 204b and side vent 220 of FIG. 2A) located disc. The sealing material can be shapeable when heated to body temperature. In use, the sealing material can be pushed and formed into the concha and external ear anatomy after the device 304 is placed as shown in FIG. 3C. The sealing material can conform to the complex anatomy of the outer ear and ensure secure fixation. The sealing material can also provide a fluid tight seal which allows the use of a slightly smaller sized device 304, which in turn allows a faster and less traumatic device insertion into the ear canal, as the sealing material is providing the primary seal instead of the device 304.

Alternatively, a fabric patch can be used in place or in conjunction with the sealing material. The fabric patch can have a disc shape and be sealably attached to the device 304, as a proximally (e.g., between sealing member 204b and side vent 220 of FIG. 2A) located disc. The fabric patch can include an adhesive, such as the temperature dependent adhesives described herein. The fabric patch can alternatively be use a conventional adhesive, for example, as used in Nexcare™ Tegaderm™ Transparent Dressing manufactured by 3M, Inc. In use, the fabric patch can be pushed and formed into the concha and external ear anatomy after the device 304 is placed as shown in FIG. 3C. The fabric patch can provide both a fluid seal and ensure secure fixation. Thus, the fabric patch can also be used with a smaller than standard device 304.

Figure 4:
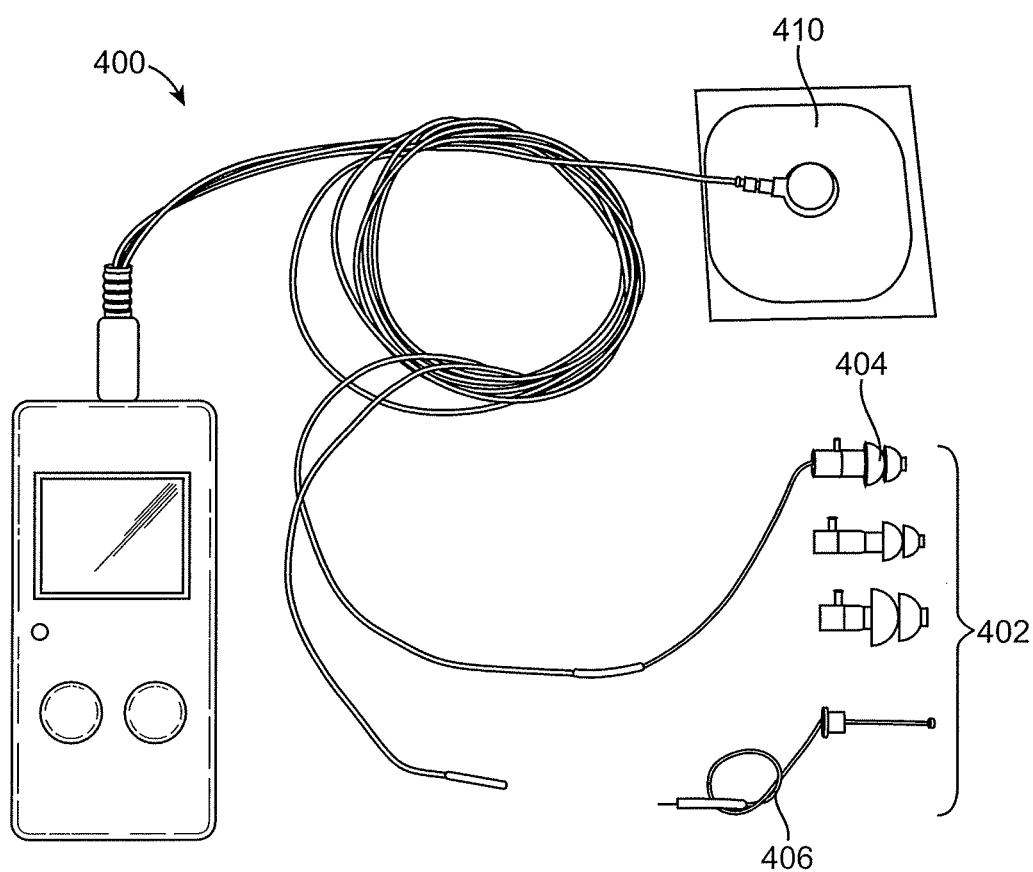
FIG. 4 shows a kit for anesthetizing a tympanic membrane, according to one embodiment of the invention.

FIG. 4 shows a kit 400 for anesthetizing a tympanic membrane of an ear of a patient using iontophoresis, according to one embodiment of the invention. The kit includes a system 402, which is substantially similar to the devices disclosed herein. Each system 402 includes an earplug 404 and an electrode device 406. As shown, various sized earplugs are possible. The kit 400 also includes a controller 408, which includes a return electrode 410, and is electrically compatible with the system 402. The controller 412 provides electrical power to the system 402 for an iontophoresis procedure. Examples of compatible controllers are shown in previously incorporated by reference and co-assigned U.S. application Ser. No. 11/962,063.

FIGS. 5A and 5B shows frontal and side views respectively, of a flexible sealing element 500 in an umbrella like configuration, according to one embodiment of the invention. Flexible sealing element 500 includes integral ribs 502 or spokes. The integral ribs 502 allow remaining portions 504 of the flexible sealing element 500 to be thinner than the ribbed portions, and thus the flexible sealing element 500 deforms very readily. Thus a device which incorporates the flexible sealing element 500, for example system 200, may achieve a seal within an ear canal with less force than a sealing element lacking the integral ribs 502. Alternatively, the integral ribs 502 may be located on the internal portion of the flexible sealing device 500.

FIGS. 5C and 5D show frontal and side views respectively, of a flexible sealing element 506, according to one embodiment of the invention. Flexible sealing element 506 includes cut out portions 508. The cut out portions 508 feature a thin web of material. The cut out portions 508 are thinner than the remaining portion 510 of the flexible sealing element 506, and thus the flexible sealing element 506 deforms very readily. Thus a device which incorporates the flexible sealing element 506, for example system 200, may achieve a seal within an ear canal with less force than a sealing element lacking the cut out portions 508. Alternatively, the cut out portions 508 may be located on the internal portion of the flexible sealing device 506.

Figure 5E:
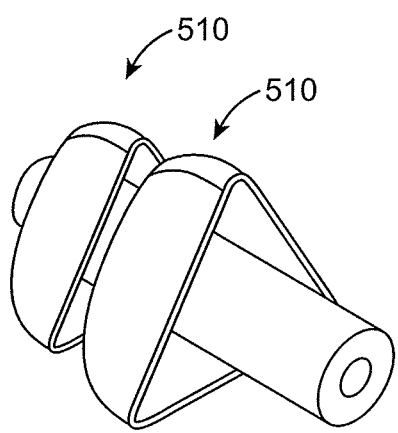
FIG. 5E shows a perspective view of a flexible sealing element, according to one embodiment of the invention.
Figure 5F:
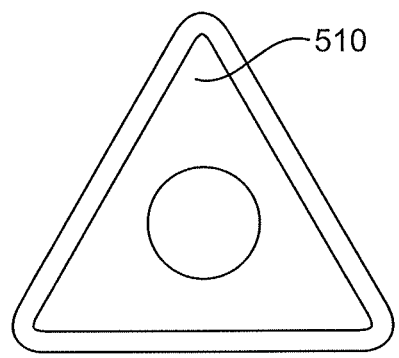
FIG. 5F shows a front view of a flexible sealing element, according to one embodiment of the invention.

FIGS. 5E and 5F show perspective and front views respectively, of a flexible sealing element 510, according to one embodiment of the invention. Flexible sealing element 506 is pyramidal or triangularly shaped, as shown. The flexible sealing element 506 includes three sides for sealing an ear canal. Ear canals do not have circular cross-sections and often are triangular in shape. Thus the flexible sealing element 510 may fit in and seal an ear canal with great effectiveness.

FIGS. 6A and 6B show rear and side views respectively, of an earplug 600, according to one embodiment of the invention. Earplug 600 includes main body 602, which may include a tubular element and at least one flexible sealing element as generally described herein. The earplug also includes ear hook 604. Previous devices have used retention mechanisms such as ear muffs or headphone style configurations to help retain earplugs. These prior devices tend to cause annoyance and discomfort to the user (e.g. small children) and result in patient induced disruptions to the iontophoresis treatment. The ear hook 604 may be formed from a flexible polymer such as silicone, and also may be integral to the earplug 600. The ear hook 604 may also include a skeleton like construction, of a flexible polymer wrapped around a core (e.g. a wire). The core may be malleable in order for the ear hook 604 may be shaped to match the profile of a specific ear. Alternatively the core may be resilient and help place a constant force from the outer ear onto the earplug 600.

FIG. 6C shows the earplug 600 in use, according to one embodiment of the invention. The ear hook 604 is designed to wrap around the crux of a helix 606 of an ear. The ear hook 604 is advantageous over other prior devices because it has relatively low mass and thus does not feel overly intrusive to a patient.

Figure 6D:
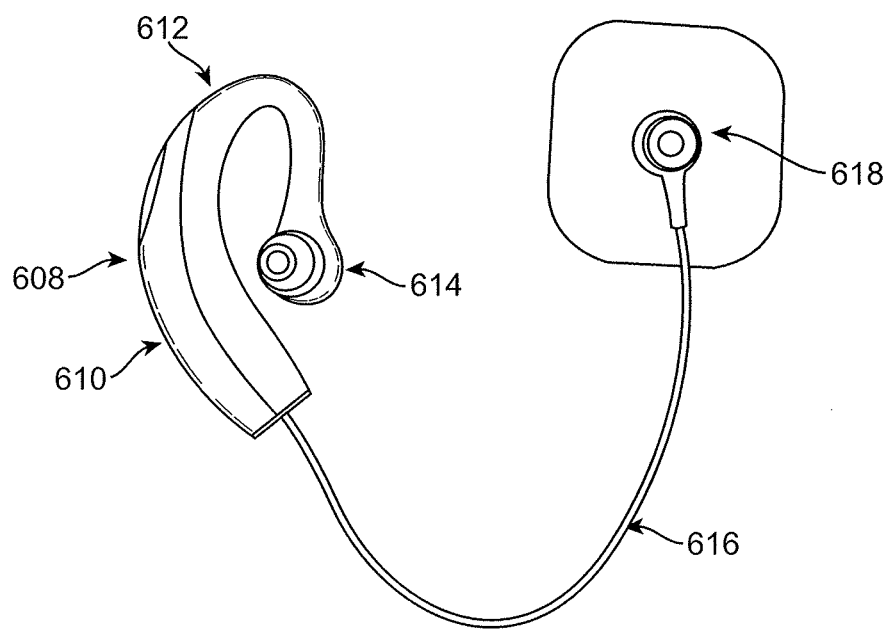
FIG. 6D shows a side view of a integrated ear bud, according to one embodiment of the invention

FIG. 6D shows an integrated ear bud 608, according to one embodiment of the invention. The ear bud includes a main body 610, which includes a power source and control unit. The control unit can have the functionality of the control unit 412 of FIG. 4. The main body 610 can include control buttons for starting or stopping an iontophoresis procedure. The main body 610 can include one or more adhesive patches. The ear bud 608 also includes a malleable bridge 612 which has a curved profile. The malleable bridge 612 can be constructed from a flexible polymer, such as rubber, and can have a malleable metal core. An earplug 614 can be pivotably connected to the malleable bridge 612. The earplug 614 can generally share the construction of the earplugs disclosed herein. A cable 616 leads from the main body 610 and connects to a return electrode 618. The return electrode 618 can include a snap element to allow connection to other return electrodes.

Figure 6E:
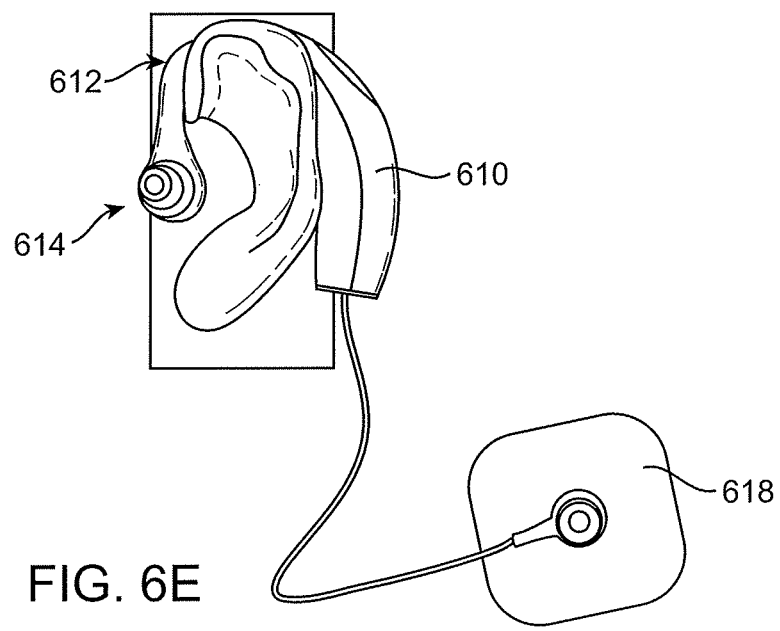
FIGS. 6E and 6F show facing views of integrated ear buds in use, according to various embodiments of the invention.

FIG. 6E shows the integrated ear bud 608 in use, according to an embodiment of the invention. The main body 610 can be placed behind the helix as shown, and can be temporarily adhered to the patient's skin. The malleable bridge 612 wraps around the helix and the earplug 614 is inserted into the ear canal. The integrated ear bud 608 supports the earplug 614 to prevent unwanted movement and to also provide a constant mounting force to help ensure a fluid tight seal. The malleable bridge 612 can be adjusted to provide more or less mounting force. The earplug 614 can be rotated so that the integrated ear bug 608 can be used on either ear. The return electrode 618 can be adhered to a portion of the patient's skin to provide an electrical return path for the control unit. As the integrated ear bud 608 includes an integrated control unit, the patient can be free to move during the procedure.

Figure 6F:
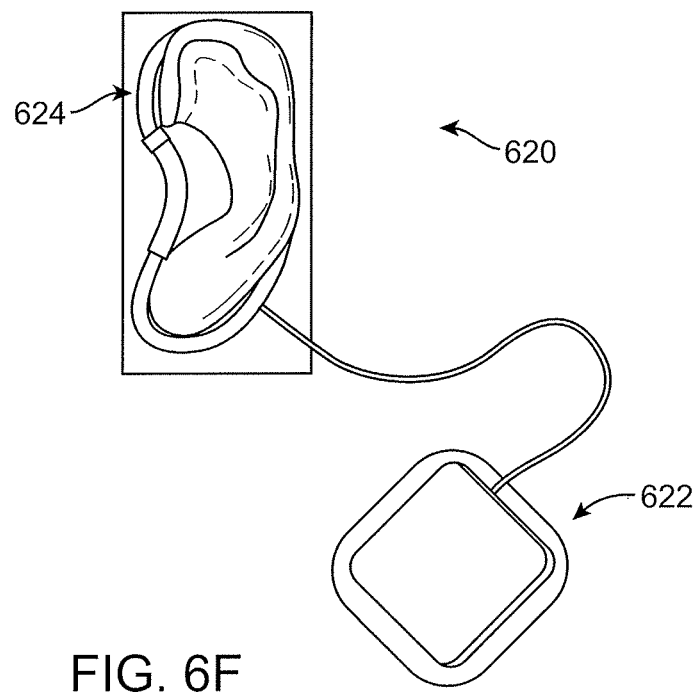

FIG. 6F shows an integrated ear bud 620 in use, according to one embodiment of the invention. The integrated ear bud 620 is configured similarly to the ear bud 608 of FIG. 6D, however, a control unit 622 is separately housed with a return electrode patch. The integrated ear bud 620 also includes a malleable body 624 which completely surrounds the helix of the ear. The malleable body 624 can be constructed from a flexible polymer, such as rubber, and can have a malleable metal core. The malleable body 624 can be adjusted to fit various ear anatomies to prevent unwanted movement and to also provide a constant mounting force to help ensure a fluid tight seal.

Figure 7A:
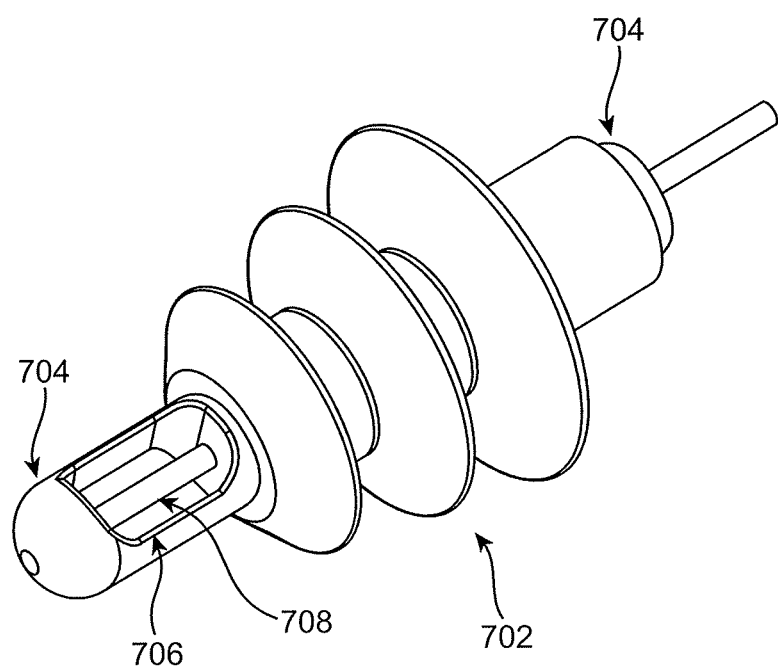
FIG. 7A shows a perspective view of an earplug, according to one embodiment of the invention.

FIG. 7A shows an earplug 700, according to one embodiment of the invention. Different regions of the ear anatomy have different levels of electrical resistance. Electrical current flows preferentially through areas of lower resistance. For example the tympanic membrane has a lower resistance than areas of cartilage in the ear canal. It is desirable to prevent unwanted electrical contact to higher resistance areas, and also desirable to limit the amount of current delivered for patient comfort. Placing the electrode as close to the tympanic membrane as possible helps achieve a positive outcome because it helps reduce overall current delivery. However, the ear canal is known to be tortuous and thus placing an electrode near the tympanic membrane is difficult without contacting other areas of the ear. The earplug 700 solves these difficulties.

The earplug 700 includes a sealing body 702 for sealing the earplug 700 in an ear canal. The sealing body 702 may include the construction of other similar earplugs disclosed herein. The sealing body 702 may or may not include lumens and vents for filling the ear canal. The earplug 700 includes an insulation body 704 which runs throughout the sealing body 702. The extended portion 706 of the insulation body 704 houses an electrode 708. The extended portion 706 is advantageous because it extends the electrode 708 well past the sealing body and closer in use to the tympanic membrane. The distal portion 706 also may contact portions of the ear canal while still providing insulation for the electrode 708.

Figure 7B:
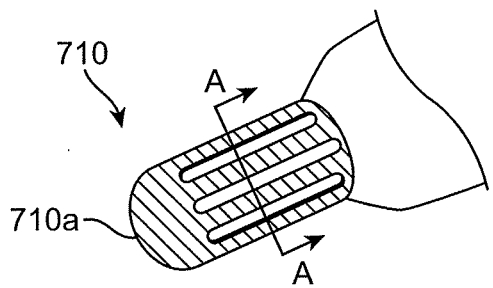
FIG. 7B shows a perspective view of an extended portion for use in an earplug, according to one embodiment of the invention.
Figure 7C:
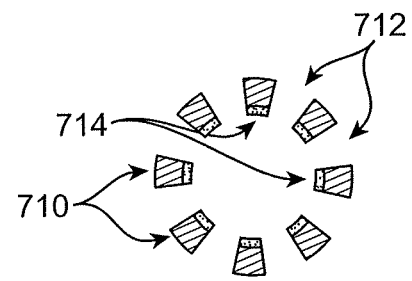
FIG. 7C shows a cross-sectional view of an extended portion for use in an earplug, according to one embodiment of the invention.

FIGS. 7B and 7C show perspective and cross-sectional views respectively, of an alternative extended portion 710, which may be used with for example the earplug 700 shown in FIG. 7A. The extended portion 710 features multiple slits 712 which provide fluid access to the inner electrode 714. The extended portion 710 may be formed from a hypotube which has been cut and coated with an external insulating barrier. The extended portion is advantageous because it reduces the amount of parts needed, and also lowers current density by using a relatively large surface area for the electrode 714. Lower current density has been found to increase patient comfort. Alternatively the domed portion may be 710 may be removed and also more or less slits 712 than shown may be used.

Figure 7D:
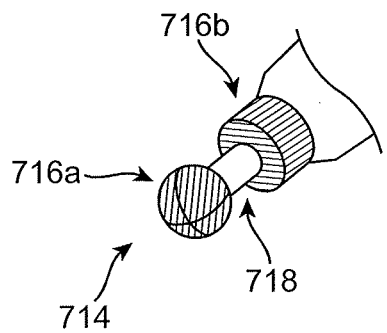
FIGS. 7D-7I show perspective views of extended portions for use in an earplug, according to various embodiments of the invention.

FIG. 7D shows a perspective view, of an alternative extended portion 710, which may be used with for example the earplug 700 shown in FIG. 7A. The extended portion 710 includes insulating portions 716a, 716b, and electrode 718. The electrode 718 may be constructed from a super elastic alloy, such as nickel titanium. And thus when electrode 716a comes into contact with portions of the ear canal, the electrode 718 will easily deflect as needed. The electrode 718 may be longer than shown, and includes multiple insulating portions 716b, to further extend the electrode 718 near the tympanic membrane.

Figure 7E:
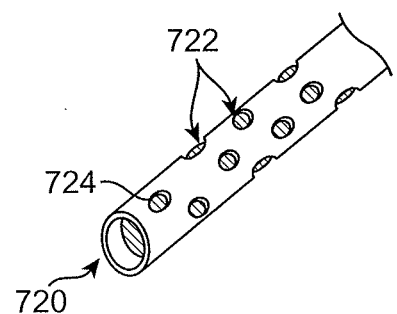

FIG. 7E shows a perspective view, of an alternative extended portion 720, which may be used with for example the earplug 700 shown in FIG. 7A. The extended portion 720 is of a hypotube construction similar to what is shown in FIGS. 7B and 7C. The extended portion 720 includes multiple drilled holes 722 which allow fluid communication with an inner electrode portion 724, shown by the darker areas. The extended portion 720 may be formed from a hypotube which has been cut and drilled, and coated with an external insulating barrier.

Figure 7F:
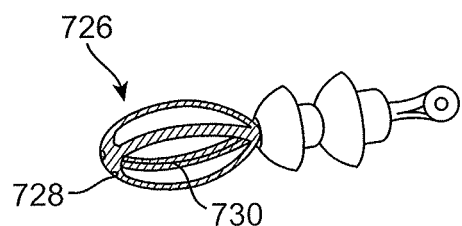

FIG. 7F shows a perspective view, of an alternative extended portion 726, which may be used with for example the earplug 700 shown in FIG. 7A. Extended portion 726 may be configured as an easily deformable but resilient basket. When the extended portion 726 comes into contact with portions of an ear canal, it will easily deflect. The extended portion 728 is constructed from an outer insulating material 728 and an inner conducting portion 730. The extended portion 726 may be constructed from a super elastic material such as nickel titanium, and of thin proportions, for example less than 0.005 inches thick.

Figure 7G:
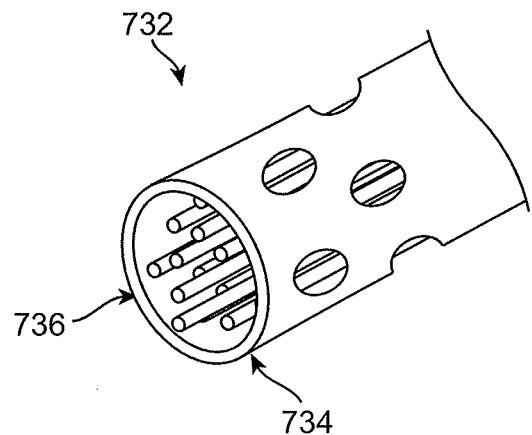

FIG. 7G shows a perspective view, of an alternative extended portion 732, which may be used with for example the earplug 700 shown in FIG. 7A. The extended portion 732 includes an outer insulating member 734 and a plurality of electrodes 736. The plurality of electrodes 736 are extended within the insulating member 734. This configuration is advantageous because it greatly increases the conductive surface area and thus helps reduce current density. This configuration also directs current flow in a distal direction towards the tympanic membrane when in use.

Figure 7H:
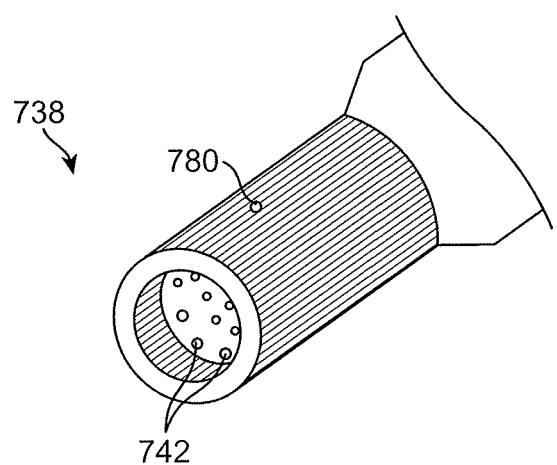

FIG. 7H shows a perspective view, of an alternative extended portion 738, which may be used with for example the earplug 700 shown in FIG. 7A. The extended portion 738 is similar to the extended portion shown in FIG. 7F. However the electrodes 742 are insulated up until a distal most point as shown. This configuration also directs current flow in a distal direction towards the tympanic membrane when in use.

Figure 7I:
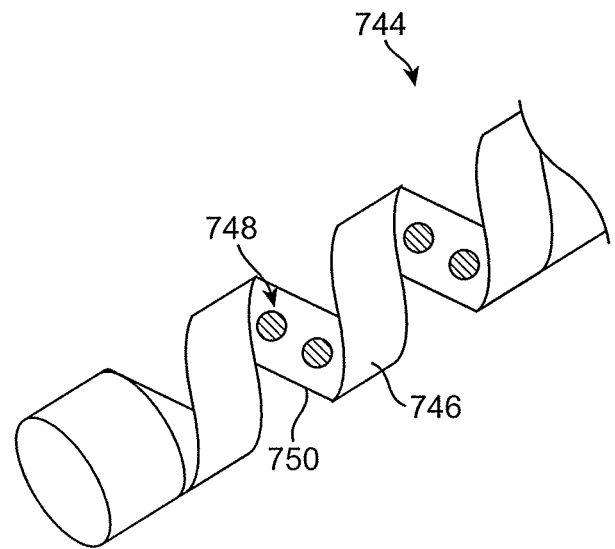
Figure 7J:
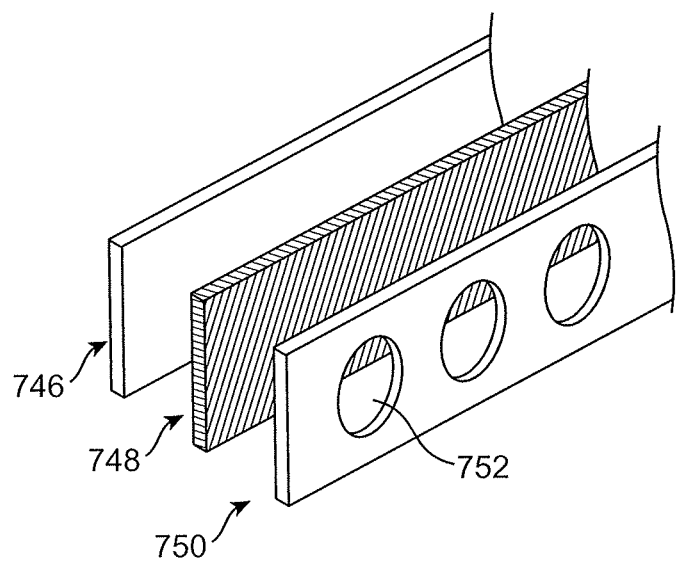
FIG. 7J shows an exploded view of an extended portion for use in an earplug, according to one embodiment of the invention.

FIGS. 7I and 7J show perspective and exploded views respectively, of an alternative extended portion 744, which may be used with for example the earplug 700 shown in FIG. 7A. The extended portion 744 includes a coiled configuration as shown, which further includes a laminated construction. The laminated construction includes an outer insulating member 746, a conducting member 748, and a inner insulating member 750. The inner insulating member 750 includes openings 752 which expose the conducting member 750. The extended portion 744 may be constructed from an initially coated flat wire, which is subsequently cut on one side to form openings 752, and further coiled into shape.

Figure 8A:
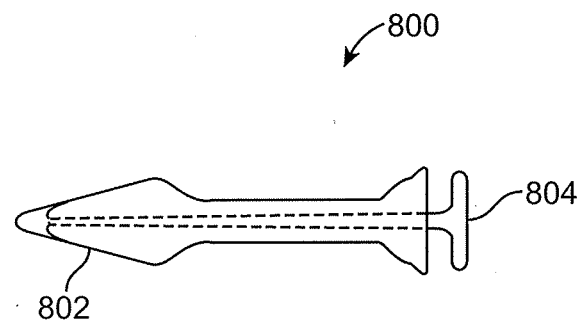
FIG. 8A shows a side view of an expandable earplug, according to one embodiment of the invention.
Figure 8B:
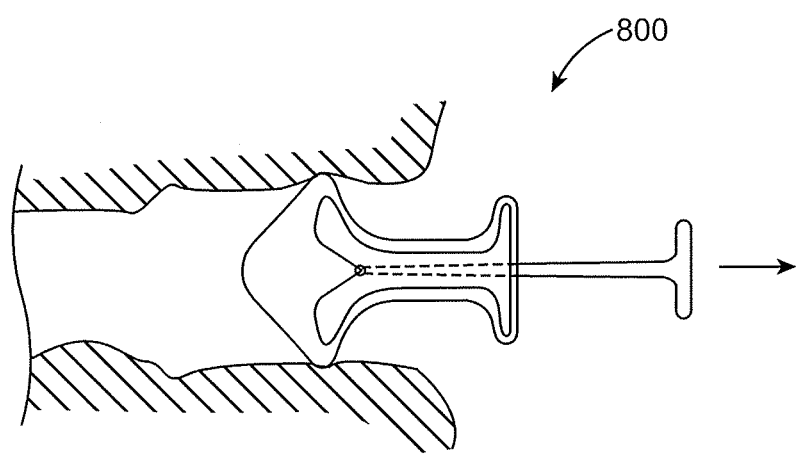
FIG. 8B shows a side view of an expandable earplug in use, according to one embodiment of the invention.

FIGS. 8A and 8B show side and operational views respectively, of an expandable earplug, according to one embodiment of the invention. Earplug 800 includes an outer expandable portion 802 and an expander 804. The outer expandable portion 802 and the expander may be connected internally near the distal end of the earplug, as shown. The expander 804 is slideable within the expandable portion, and may be withdrawn proximally to force the outer expandable portion to expand into a second configuration, as shown in FIG. 8B. The outer expandable portion 802 may be constructed from a soft polymer, for example silicone. This configuration is advantageous because it allows for a precise fit within the anatomy of a specific ear, and also allows deeper positioning.

Figure 9A:
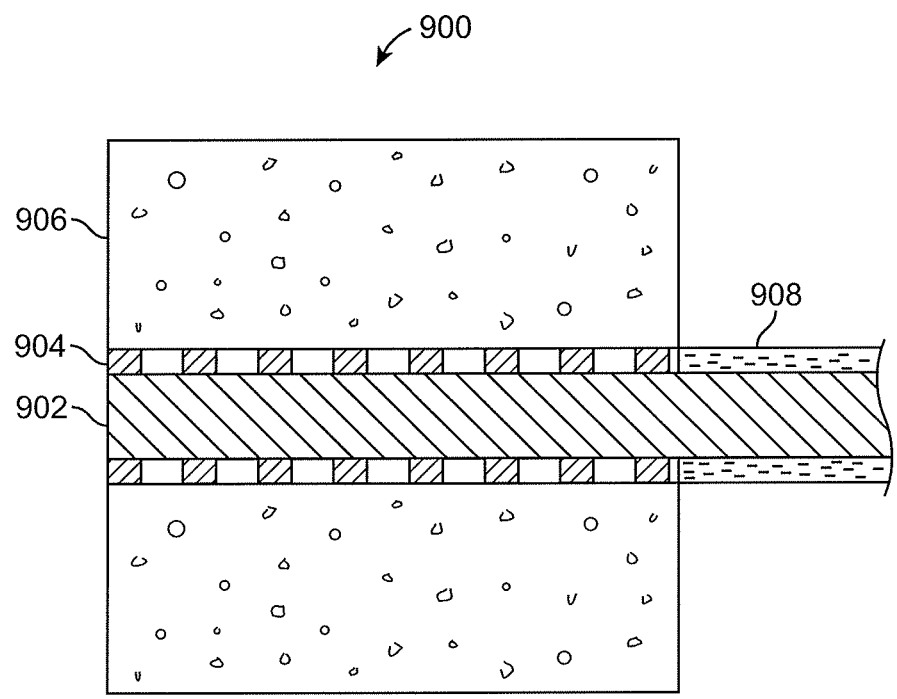
FIG. 9A shows a cross-sectional view of a foam plug device, according to one embodiment of the invention.

FIG. 9A shows a foam plug device 900, according to one embodiment of the invention. The foam plug device 900 includes an electrode 902 and a perforated tube 904 attached to the electrode 902. A foam plug 906 surrounds the electrode 902. The foam plug 906 can have a cylindrical or conical shape, and can be constructed from open celled foam. The electrode 902 can be constructed from a malleable metal (e.g., silver) solid or stranded wire, or a solid or perforated tube, and include insulation 908 leading from the proximal end of the perforated tube 904. An electrical connector (not shown) can connect to the proximal end of the electrode 902. The perforated tube 904 can be constructed from a flexible and insulative or conductive material, and generally includes perforations throughout. The foam plug device 900 can also include additional sealing elements (not shown) and/or adhesives, as described herein. In use, the foam plug 906 can be compressed, inserted into an ear canal, and then allowed to expand to seal the ear canal. Drug solution can be introduced into the ear canal prior to insertion of the foam plug device 900, or after due to the open cell nature of the foam plug 902. The porosity of the foam plug can allow drug solution contact throughout the length of the perforated tube 904, thereby increasing electrode surface area via the perforations in the perforated tube 904. The porosity of the foam plug can also prevent pressure build-up during an iontophoresis procedure.

Figure 9B:
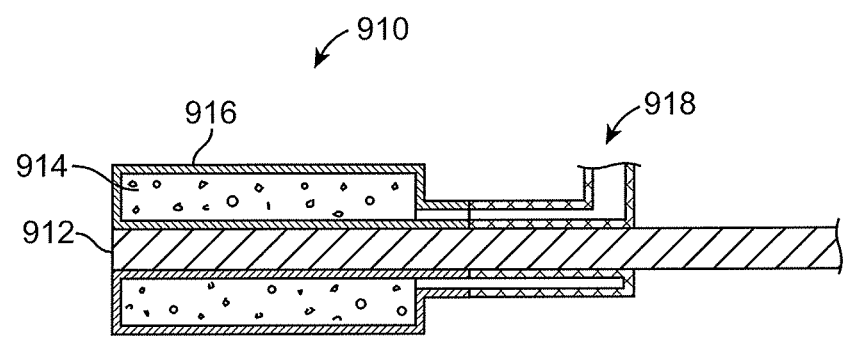
FIG. 9B shows a cross-sectional view of a foam balloon device, according to an embodiment of the invention.

FIG. 9B shows a foam balloon device 910, according to one embodiment of the invention. The foam balloon device 910 includes an electrode 912. The electrode 912 can be constructed from a malleable metal (e.g., silver) solid or stranded wire, or solid or perforated tube. In one embodiment, the electrode 912 may include an outer lumen (not shown) which can be manufactured from a polyether block amide (e.g., Pebax® 55D) with an inner diameter of about 0.060" and an outer diameter of about 0.072". An electrical connector (not shown) can connect to the proximal end of the electrode. The electrode 912 can also include a distal end with an expanded insulator surrounding a plurality of wire strands. A foam plug 914 surrounds the electrode 912. The foam plug 914 may be constructed from open celled foam. A polyether foam (EC85HDE) with a density of 5 lb/ft$^3$, and manufactured by Foamex Innovations, Inc. has been found to be suitable. The foam plug can have a cylindrical shape with an outer diameter of 5-15 mm, and an inner diameter of 2.5 mm. Outer diameters of 8.3 mm and 11 mm have been used. The foam plug can have other shapes, such as conical. The foam plug is encased by a double walled balloon 916. The double walled balloon 916 can be constructed from a compliant, semi-compliant, or non-compliant material. In one embodiment, the double walled balloon 916 can be formed by dip coating a shaped mandrel with a silicone, such as MED10-6400 manufactured by NuSil Technology LLC. The double walled balloon 916 can then be adhered to a portion of the electrode 912 and then partially inverted to create a double wall. The foam plug 914 can then be inserted into the space between the walls. The distal portion of the balloon 916 can be connected to a suction coupler 918, such as T connector 88207 available from Qosina Corp.

In use, a vacuum can be applied to the suction coupler 918, which causes the foam plug 914 to collapse. The foam balloon device 910 can then be inserted into an ear canal. Once in place, the vacuum can be discontinued which causes the foam 914 to expand. The foam 914 expansion presses the double walled balloon 916 in contact with the ear canal walls to fluidly seal drug solution within the ear canal. As positive air pressure is not used to inflate the double walled balloon, the danger of balloon rupture is negated. Vacuum may be reapplied to re-collapse the foam 914 in order to aid in removal.

Figure 10A:
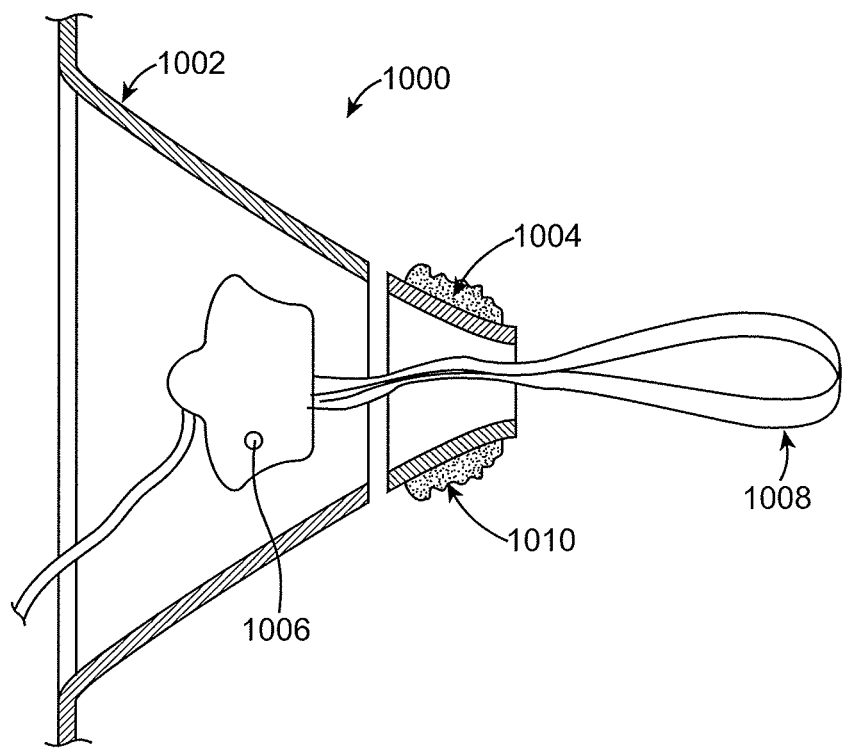
FIG. 10A shows a cross-sectional view of speculum port, according to an embodiment of the invention.

FIG. 10A shows a speculum port 1000, according to an embodiment of the invention. The speculum port 1000 can have a generally conical shape. The speculum port 1000 can be constructed from a polymer or metal alloy. The speculum port 1000 may be relatively flexible or stiff. The speculum port 1000 can include a proximal port 1002 which is removably coupled to a distal port 1004. The proximal port 1002 can be coupled to the distal port 1004 by a slight interference fit or by a threaded connection. An inner plug 1006 can be removably and sealably coupled to the distal port 1004. The inner plug 1006 includes an electrode 1008, which is configured as a looped electrode as shown in FIG. 2F. However, the electrode 1008 can generally take the form of any of the electrodes disclosed herein. The inner plug 1006 can include sealing members (not shown) configured similarly to other sealing members disclosed herein. The distal port 1004 can include an adhesive layer 1010 which may take the form of any of the adhesives disclosed herein. The adhesive layer 1010 may also be a layer of pliable silicone putty, ostomy bag adhesive gasket material, expanding foam, impression material, gel, bone wax, balloon cement, or a silicone gasket.

Figure 10B:
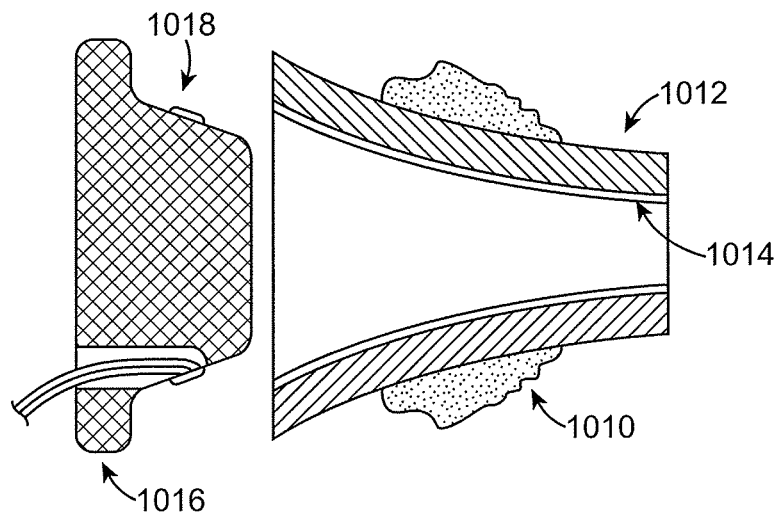
FIG. 10B shows a cross-sectional view an alternative distal port, according to one embodiment of the invention.

FIG. 10B shows an alternative distal port 1012, according to one embodiment of the invention. The distal port 1012 is configured similarly to distal port 1004, however, distal port 1012 includes an electrode surface 1014. The electrode surface 1014 can be a layer of metal, such as silver, coupled to the interior surface of the distal port 1004. An inner plug 1016 can removably and sealably couple to the distal port 1012. The inner plug 1016 can include contact surface 1018 which can make electrical contact with the electrode surface when the inner plug 1016 couples to the distal port 1004.

Figure 10C:
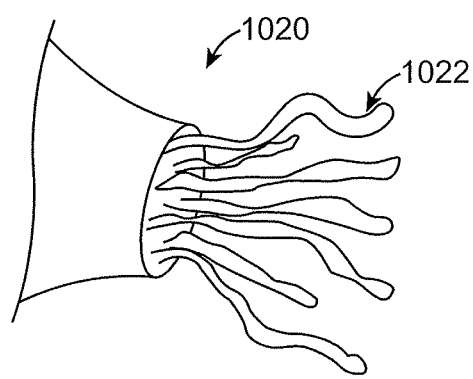
FIG. 10C shows a perspective view of an alternative distal port, according to one embodiment of the invention

FIG. 10C shows an alternative distal port 1020, according to one embodiment of the invention. The distal port 1012 is configured similarly to distal port 1004, however, distal port 1012 couples to a plug with a plurality of tentacle electrodes 1022. The tentacle electrodes 1022 are highly flexible and provide increased surface area. The tentacle electrodes 1022 can include insulative and conductive areas of exposed metal.

Figure 10D:
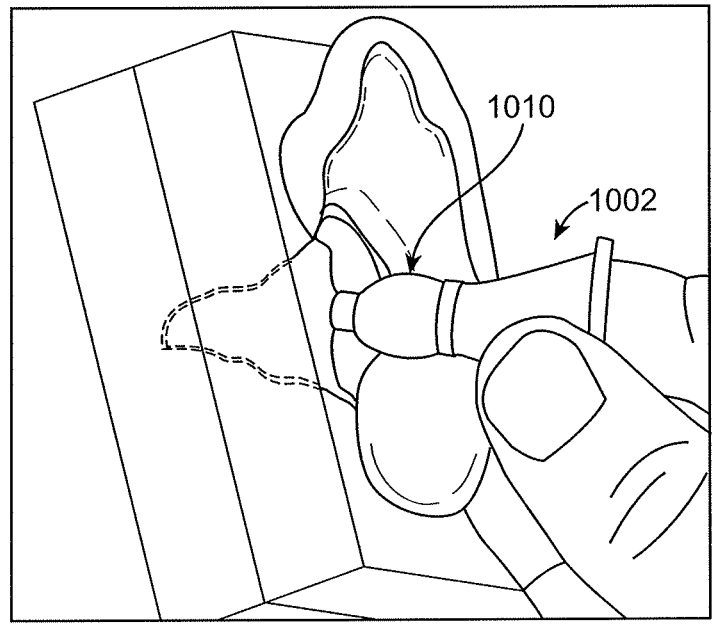
FIGS. 10D and 10E show a speculum port in use, according to one embodiment of the invention.
Figure 10E:
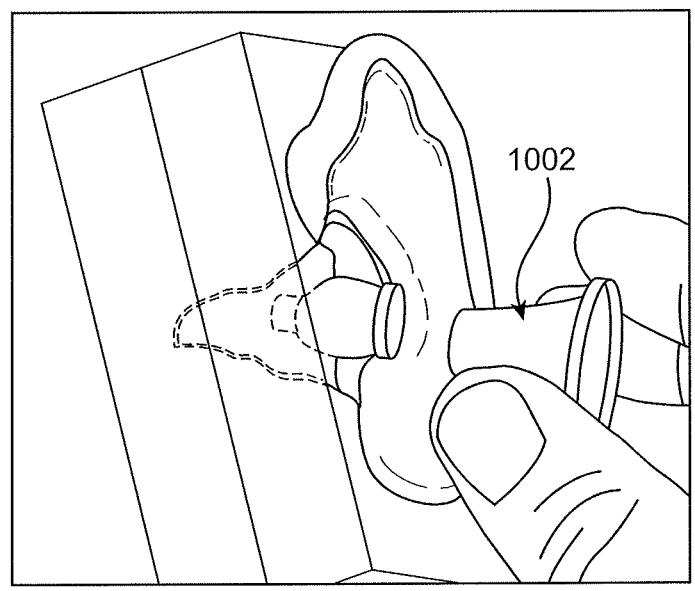

FIGS. 10D and 10E show the speculum port 1000 in use, according to one embodiment of the invention. The speculum port 1000 can be handled by the proximal port 1002. The increased diameter of the proximal port 1002 allows for finger manipulation and insertion of the speculum port 1000. The speculum port can be adjusted to provide visualization of the tympanic membrane. The adhesive layer 1010 on the distal port 1004 provides a fluid tight seal and fixation between the distal port 1004 and the ear canal. Once the speculum port 1000 has been placed in an optimal position, the proximal port 1002 can be decoupled from the distal port 1004. The distal port 1004 can then be filled with a drug solution and the inner plug 1006 can be inserted into the distal port 1004. The inner plug 1006 can then be supplied with electrical current to complete the iontophoresis procedure.

Figure 10F:
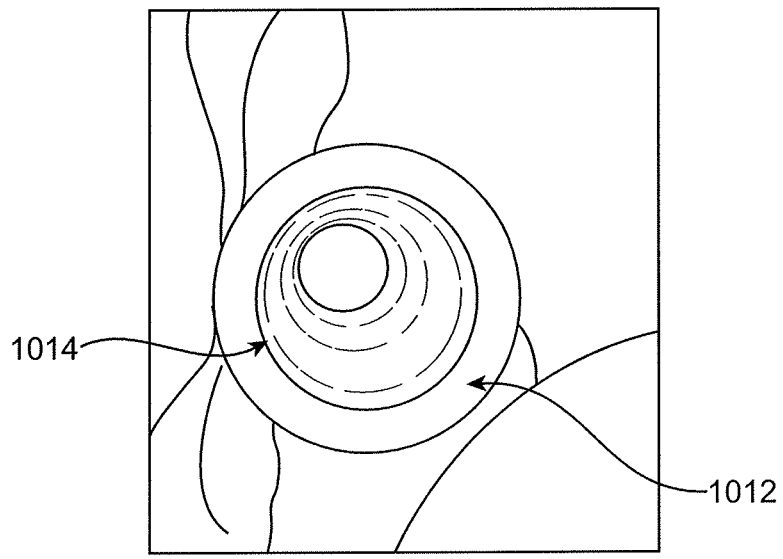
FIGS. 10F through 10H show a speculum port in use, according to one embodiment of the invention.
Figures 10G, 10H:
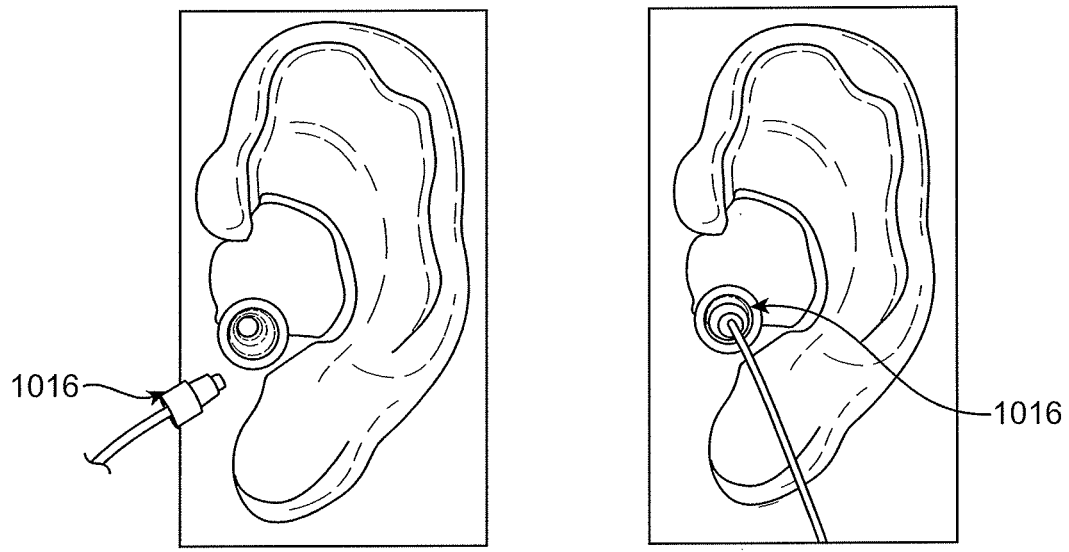

FIGS. 10F through 10H show the speculum port 1000 in use, according to one embodiment of the invention. The speculum port 1000 includes alternative distal port 1012 with electrode surface 1014. The distal port 1012 has already been placed in the ear canal and the proximal port 1002 has been removed, in accordance with FIGS. 10D and 10E. The distal port 1012 can be filled with a drug solution, and the inner plug 1016 can be inserted into the distal port 1012. The inner plug 1016 can then be supplied with electrical current to complete the iontophoresis procedure.

Figure 11:
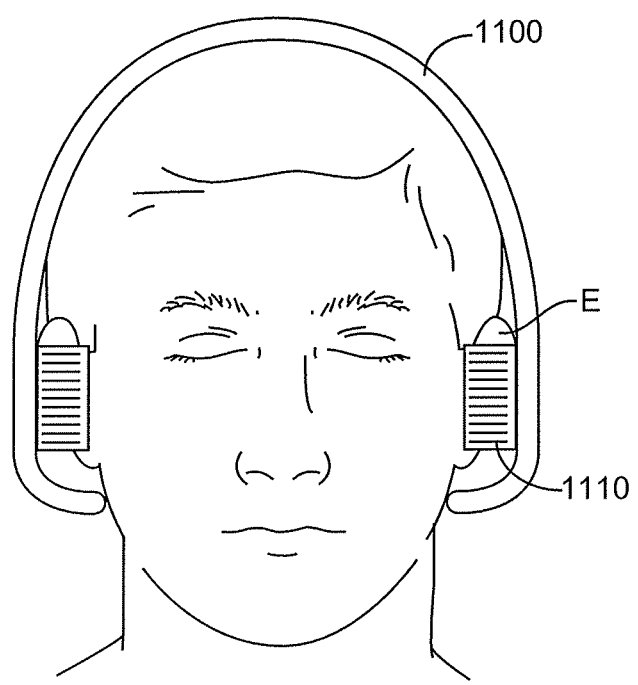
FIGS. 11 and 12 illustrate simplified support structures that are worn on a patient's head and support an iontophoresis system, according to various embodiments of the invention.

FIG. 11 shows a simplified support structure 1100 that is worn on the patient's head, according to one embodiment of the invention. The simplified support structure 1100 is worn on the patient's head while the patient is awake and upright. The support structure 1100 is configured to hold the one or more systems described herein in alignment with the patient's ears E. As can be seen in FIG. 11, the support structure 1100 can have an alignment structure with a first body 1110 engaging the first ear, a second body 1110 engaging the second ear, and a member extending around the head of the patient between the first and second body. Any of the earplugs of the present invention may be coupled to the head via a headset as in FIG. 11.

Figure 12:
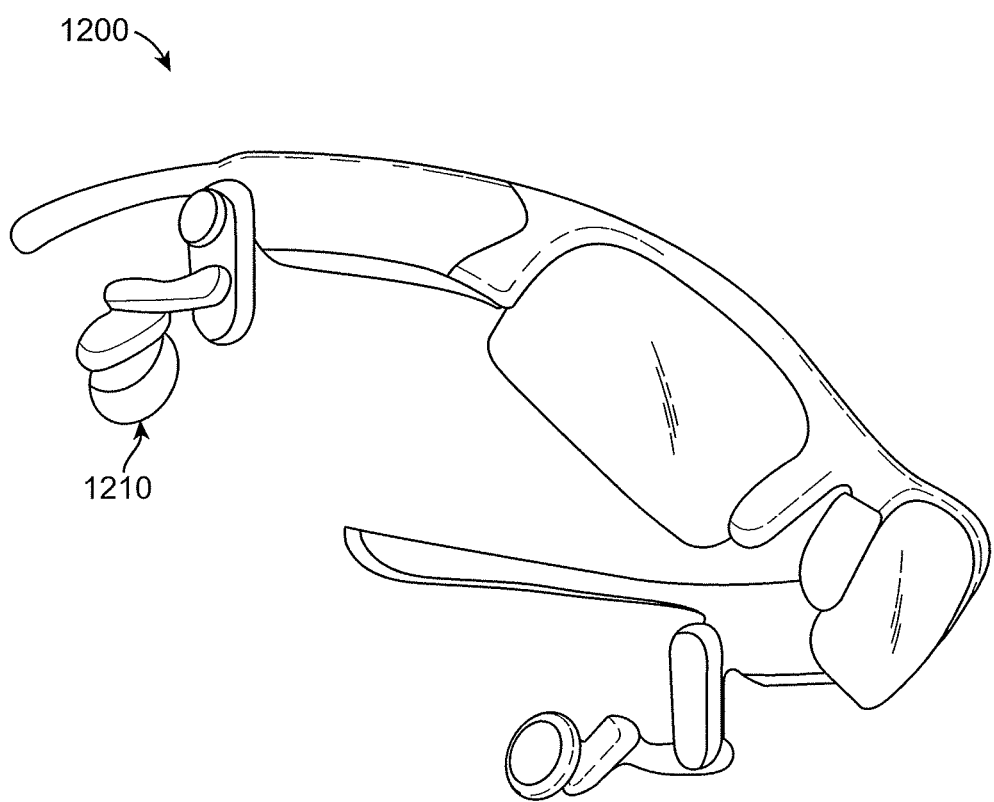

FIG. 12 shows a simplified support structure 1200 that is worn on the patient's head, according to one embodiment of the invention. The support structure 1200 is configured similarly to eyeglasses and can be worn in a similar fashion. Earplugs 1210 are hingably connected to the support structure 1200 and can be leveraged into ear canals by the support structure 1200. The earplugs 1210 can be configured similarly to any of the earplugs disclosed herein. The support structure 1200 can prevent unwanted movement and provide sealing force against the earplugs 1210. The support structure 1200 can include adjustable elements to adjust width and length for various sized patients. The support structure 1200 can include visual panels, such as LCD panels which can provide video viewing for the patient. The earplugs 1210 can also include speakers to supply audio to the patient.

The present invention may be embodied in other specific forms without departing from the essential characteristics thereof. These other embodiments are intended to be included within the scope of the present invention, which is set forth in the following claims.

What is claimed is:

1. A system for use in iontophoretic substance delivery to a tympanic membrane of an ear of a human or animal subject, the system comprising:
   (a) an earplug including:
      (i) a distal portion;
      (ii) a proximal portion;
      (iii) a tube extending from the distal portion to the proximal portion, the tube defining a lumen; and
      (iv) at least one flexible sealing element extending from an outer surface of the tube, wherein a first flexible sealing element of the at least one flexible sealing element includes:
         (A) an external facing; and
         (B) an adhesive layer configured on the external facing; and
   (b) an electrode device including:
      (i) an elongate shaft, and
      (ii) an electrode tip having a diameter greater than that of the elongate shaft, the elongate shaft of the electrode device at least partially disposed within the lumen of the tube of the earplug, the electrode device being movable within the lumen of the tube of the earplug between a retracted position, in which fluid can pass around the electrode device through the lumen, and an advanced position, in which the electrode tip contacts an inner surface of the tube to prevent fluid from flowing through the lumen.

2. The system of claim 1, wherein the tube has a stiffness less than a stiffness of the proximal and distal portions of the earplug and wherein the flexible sealing element is disposed closer to the distal portion than to the proximal portion.

3. The system of claim 1, wherein the earplug further comprises a side vent in fluid communication with the lumen of the tube for allowing venting of air and/or fluid from the tube.

4. The system of claim 1, wherein the distal portion is rigid relative to the tube.

5. The system of claim 1, wherein the distal portion includes an o-ring, the o-ring configured to form a seal with the electrode tip of the electrode device when the electrode device is in the advanced position.

6. The system of claim 5, wherein an outer diameter of the electrode tip is greater than an internal diameter of the o-ring, and wherein the o-ring is flexible such that the electrode tip can pass into the o-ring to form the seal.

7. The system of claim 1, wherein the first flexible sealing element is umbrella shaped, with an open end of the first flexible sealing element facing the proximal portion of the earplug.

8. The system of claim 1, wherein the first flexible sealing element is a distal sealing element, wherein a second flexible sealing element of the at least one flexible sealing element is a proximal sealing element, and wherein a diameter of the proximal sealing element is larger than a diameter of the distal sealing element.

9. The system of claim 8, wherein each of the first flexible sealing element and the second flexible sealing element is umbrella shaped, with an open end of each flexible sealing element facing the proximal portion of the earplug.

10. The system of claim 1, wherein the electrode device is malleable.

11. The system of claim 1, additionally comprising an ear hook connected with the proximal portion of the earplug, the ear hook including a curved member for engaging a portion of the ear and preventing dislodgement of the earplug after placement in the ear.

12. The system of claim 1, further comprising an additional earplug and an additional electrode device for use in iontophoretic substance delivery to a tympanic membrane of another ear of the human or animal subject.

13. The system of claim 12, further comprising a headset for coupling the earplug and the additional earplug while they are in the subject's ears.

14. A system for use in iontophoretic substance delivery to a tympanic membrane of an ear of a human or animal subject, the system comprising:
   (a) an earplug including:
      (i) an elongate, flexible tube with a proximal portion, a distal portion, and a main lumen extending therethrough;
      (ii) a first flexible sealing element shaped like an umbrella to form a seal within an ear canal, wherein the first flexible sealing element comprises an external facing with an adhesive layer, the first flexible sealing element being integral to and disposed on an exterior of the elongate, flexible tube and being offset a distance from a most distal end of the distal portion of the elongate, flexible tube;
      (iii) a fitting coupled with the proximal portion of the elongate, flexible tube and including a side vent in fluid communication with the main lumen; and
      (iv) a stiffening tube located within the distal portion of the elongate, flexible tube distal to the first flexible sealing element, the stiffening tube preventing the distal portion of the elongate, flexible tube from bending; and
   (b) an electrode device including:
      (i) an elongate shaft; and
      (ii) an electrode tip having a diameter greater than that of the elongate shaft.

15. The system of claim 14, the earplug further comprising:
   (v) a second flexible sealing element shaped like an umbrella to form a seal within the ear canal, the second flexible sealing element being integral to and disposed on the exterior of the elongate, flexible tube and being proximal to the first sealing element.

16. The system of claim 14, further comprising a kit, the kit comprising:
   (i) a controller connected to the electrode device;
   (ii) an additional earplug for another ear of the subject; and
   (iii) an additional electrode device for the additional earplug,
   wherein the controller connects to the electrode device and the additional electrode device.

17. The system of claim 14, further comprising a headset for placing on the subject's head and holding the electrode device and the earplug.

18. The system of claim 14, further comprising a drug solution to provide iontophoretic anesthesia to the tympanic membrane of the ear of the subject.

19. The system of claim 18, further comprising a drug delivery device for delivering the drug solution into the ear canal of the subject.

20. A system for use in iontophoretic substance delivery to a tympanic membrane of an ear of a human or animal subject, the system comprising:
   (a) an earplug including:
      (i) a distal portion;
      (ii) a proximal portion;
      (iii) a tube extending from the distal portion to the proximal portion, the tube defining a lumen; and
      (iv) at least one flexible sealing element extending from an outer surface of the tube, wherein a first flexible sealing element of the at least one flexible sealing element includes:
         (A) an external facing; and
         (B) an adhesive layer configured on the external facing; and
   (b) an electrode device including:
      (i) an elongate shaft, and
      (ii) an electrode tip having a diameter greater than that of the elongate shaft, the elongate shaft of the electrode device being at least partially disposed within the lumen of the tube of the earplug, the electrode device being configured to selectively allow fluid communication through the lumen of the tube between the distal portion and the proximal portion of the earplug, an inner surface of the tube and an outer surface of the electrode tip being configured to provide feedback when the electrode device transitions between an advanced position and a retracted position.

* * * * *